(12) United States Patent
Takasugi et al.

(10) Patent No.: US 8,582,218 B2
(45) Date of Patent: Nov. 12, 2013

(54) ENDOSCOPE FOR OBLIQUE VIEWING

(75) Inventors: Yoshiharu Takasugi, Iruma (JP); Daisuke Akiyama, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 963 days.

(21) Appl. No.: 12/563,248

(22) Filed: Sep. 21, 2009

(65) Prior Publication Data

US 2010/0076268 A1 Mar. 25, 2010

(30) Foreign Application Priority Data

Sep. 19, 2008 (JP) ................................. 2008-240676

(51) Int. Cl.
*G02B 9/00* (2006.01)

(52) U.S. Cl.
USPC .......................................................... 359/754

(58) Field of Classification Search
USPC .................. 359/642, 754–756, 763, 771, 784
See application file for complete search history.

(56) References Cited

U.S. PATENT DOCUMENTS

| | | | |
|---|---|---|---|
| 4,037,938 A * | 7/1977 | Yamashita et al. | 359/734 |
| 4,877,314 A | 10/1989 | Kanamori | |
| 5,569,162 A | 10/1996 | Komi | |
| 7,160,249 B2 * | 1/2007 | Hasegawa | 600/167 |
| 7,280,283 B1 | 10/2007 | Kasai | |

FOREIGN PATENT DOCUMENTS

| | | |
|---|---|---|
| JP | 62-65010 A | 3/1987 |
| JP | 63-291019 A | 11/1988 |
| JP | 05-113541 | 5/1993 |
| JP | 07-294806 | 11/1995 |
| JP | 08-076028 | 3/1996 |
| JP | 63-57617 U | 4/1998 |
| JP | 10-113329 | 5/1998 |
| JP | 11-216102 A | 8/1999 |
| JP | 2004-226722 | 8/2004 |
| JP | 2005-95432 A | 4/2005 |
| JP | 2005-287851 | 10/2005 |

* cited by examiner

*Primary Examiner* — James Greece
(74) *Attorney, Agent, or Firm* — Scully, Scott, Murphy & Presser, P.C.

(57) ABSTRACT

An endoscope for oblique viewing including an image pickup device, a front lens group having a positive refractive power, a prism disposed on the CCD side of the front lens group, and a rear lens group disposed on the CCD side of the prism and having a positive refractive power.

40 Claims, 32 Drawing Sheets

$\alpha = 45°$

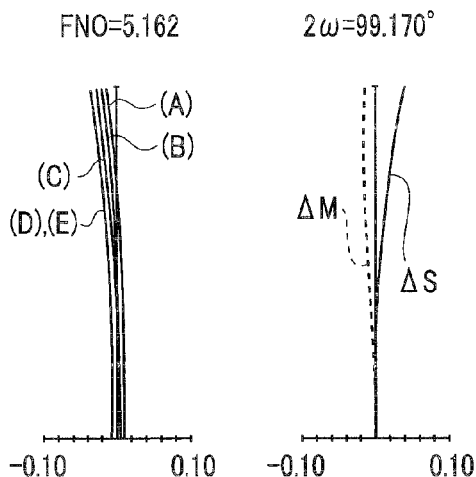
FIG. 18A
FNO=5.162
FIG. 18B
2ω=99.170°
FIG. 18C
FIG. 18D
2ω=99.170°
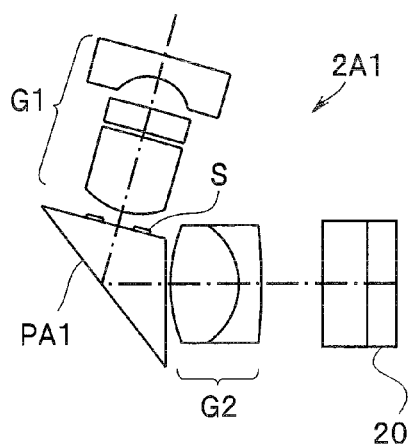
FIG. 19
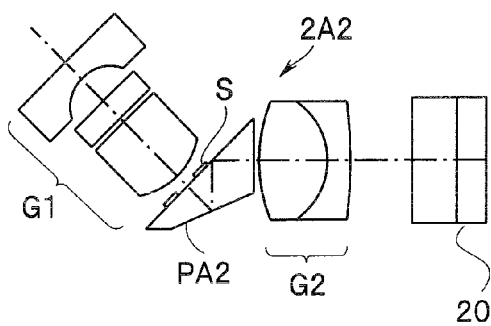
FIG. 20

FNO=5.099

2ω=99.202°

2ω=99.202°

2ω=99.202°

FNO=4.823

2ω=97.762°

2ω=97.762°

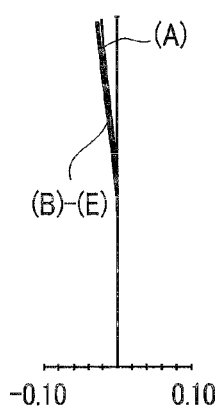
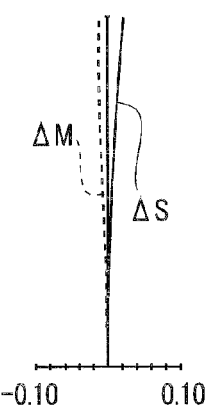
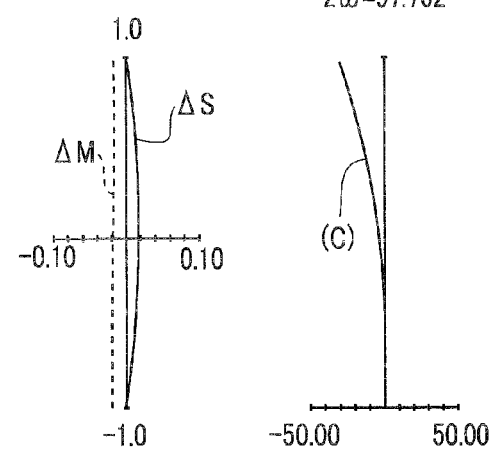
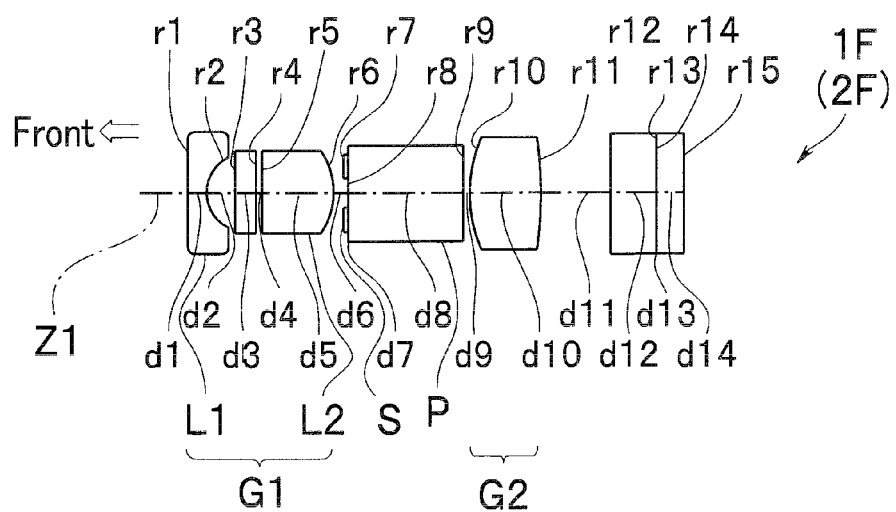

FNO=5.087

2ω=99.078°

2ω=99.078°

2ω=99.078°

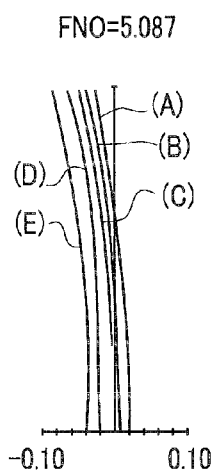
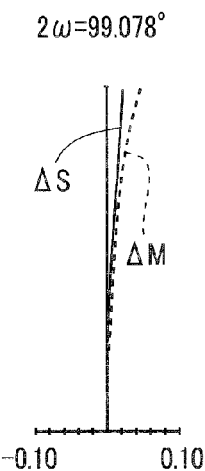
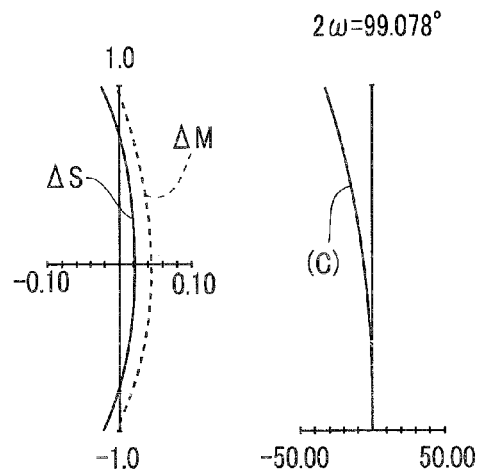
FIG. 33A  FIG. 33B  FIG. 33C  FIG. 33D
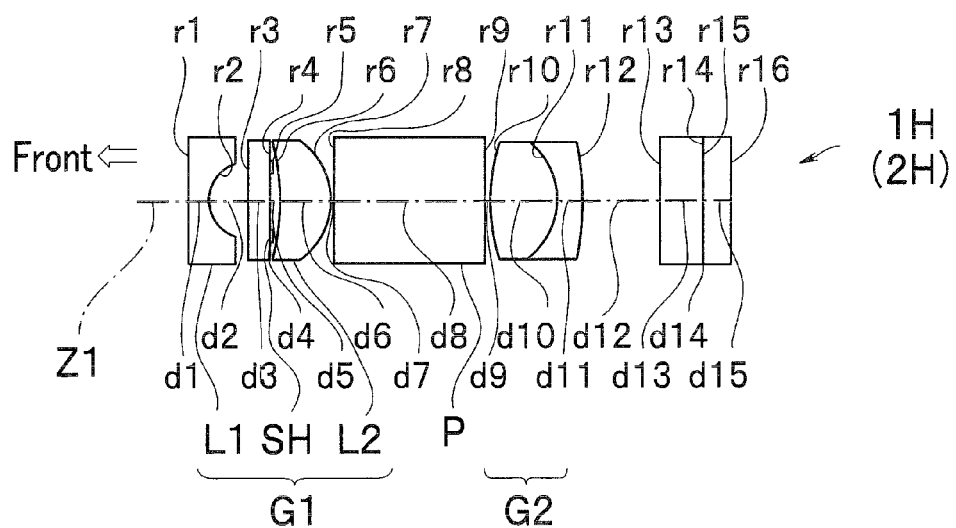
FIG. 34

FNO=5.276

2ω=99.148°

2ω=99.148°

FIG. 38
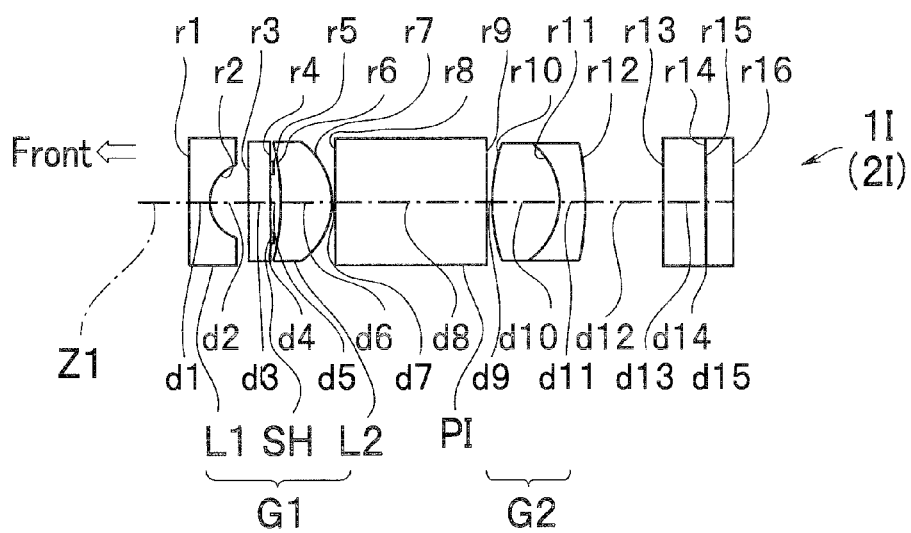
FIG. 39A
FNO=5.276
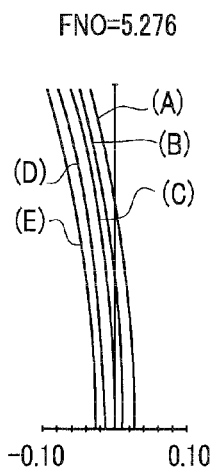
FIG. 39B
2ω=99.182°
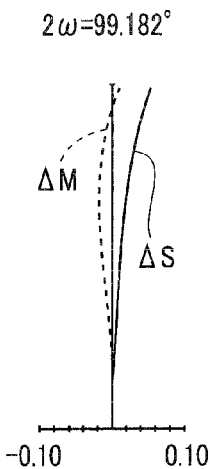
FIG. 39C
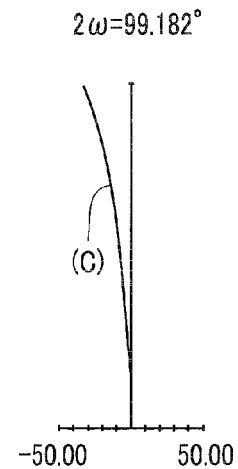
FIG. 39D
2ω=99.182°

FNO=5.290

2ω=99.238°

2ω=99.238°

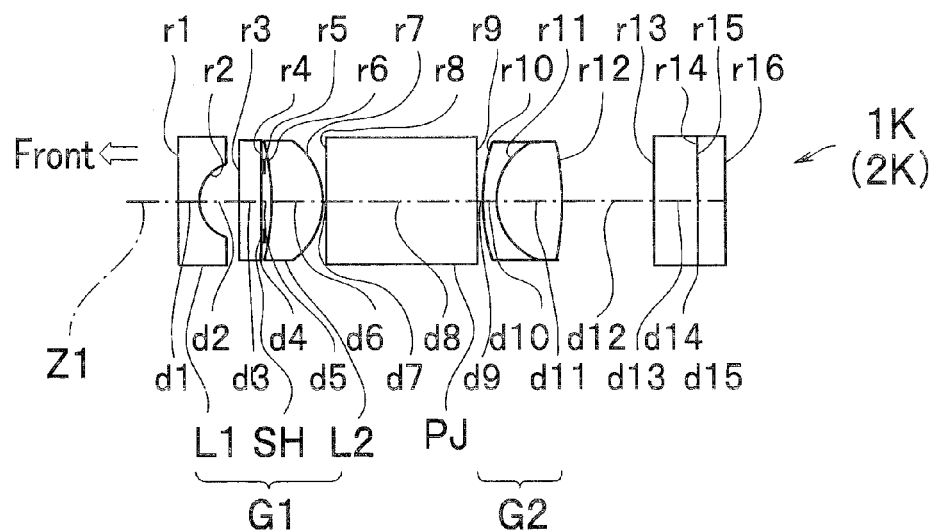
FIG. 42
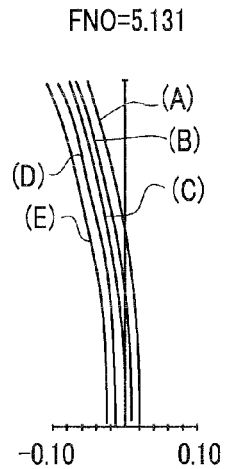
FIG. 43A
FNO=5.131
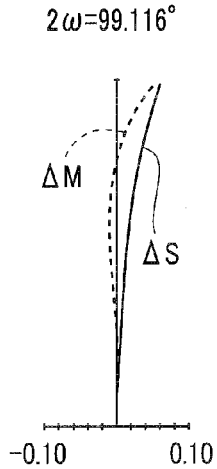
FIG. 43B
2ω=99.116°
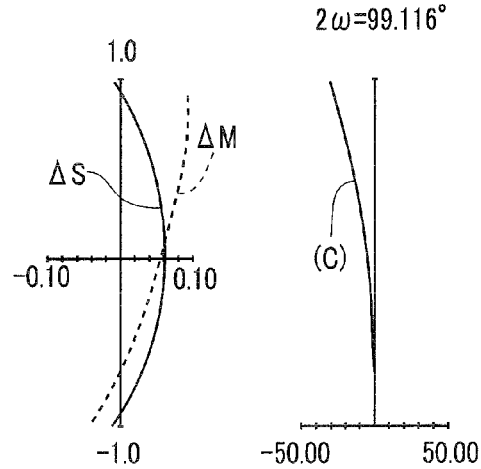
FIG. 43C
FIG. 43D
2ω=99.116°

FNO=4.807

| Example | d/f | d/IH | D1/f | D2/f | D1/D2 | \|f1\|/f | f2/f | G1f/f | G2f/f | G1f/G2f |
|---|---|---|---|---|---|---|---|---|---|---|
| 1 | 1.526 | 1.949 | 2.138 | 2.914 | 0.734 | 0.778 | 1.957 | 3.170 | 3.775 | 0.840 |
| 2 | 1.338 | 1.704 | 2.145 | 2.820 | 0.761 | 0.791 | 1.882 | 2.517 | 4.162 | 0.605 |
| 3 | 1.474 | 1.917 | 2.127 | 2.927 | 0.727 | 0.866 | 2.190 | 5.494 | 3.208 | 1.712 |
| 4 | 1.412 | 1.808 | 2.102 | 3.141 | 0.669 | 0.887 | 2.202 | 3.973 | 3.430 | 1.158 |
| 5 | 1.310 | 1.670 | 2.149 | 3.222 | 0.667 | 0.816 | 2.037 | 3.270 | 3.389 | 0.965 |
| 6 | 1.485 | 1.892 | 2.169 | 2.553 | 0.850 | 0.756 | 1.695 | 1.759 | 4.996 | 0.352 |
| 7 | 1.457 | 1.857 | 2.164 | 2.594 | 0.834 | 0.774 | 1.670 | 1.721 | 3.738 | 0.461 |
| 8 | 1.530 | 1.969 | 1.844 | 3.085 | 0.598 | 0.722 | 1.947 | 3.377 | 3.960 | 0.853 |
| 9 | 1.447 | 1.859 | 1.852 | 3.089 | 0.599 | 0.721 | 1.932 | 3.192 | 4.076 | 0.783 |
| 10 | 1.344 | 1.723 | 1.847 | 3.095 | 0.597 | 0.717 | 1.907 | 3.067 | 4.163 | 0.737 |
| 11 | 1.542 | 1.969 | 1.838 | 3.043 | 0.604 | 0.753 | 1.982 | 3.364 | 3.916 | 0.859 |
| 12 | 1.644 | 1.969 | 2.014 | 3.238 | 0.622 | 0.761 | 2.138 | 3.807 | 3.950 | 0.964 |
| 13 | 1.705 | 1.951 | 2.549 | 2.964 | 0.860 | 0.892 | 2.300 | 3.392 | 3.862 | 0.878 |

FIG. 49
FIG. 50
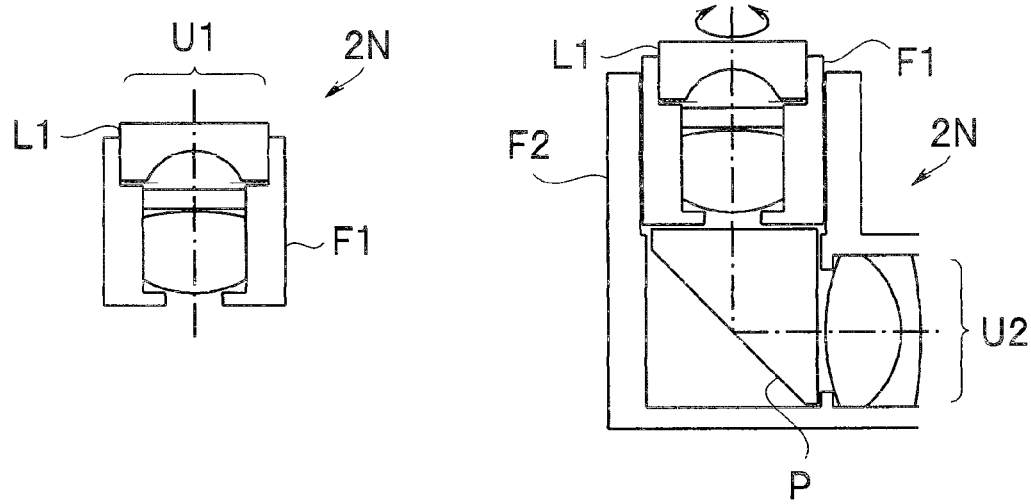
FIG. 51
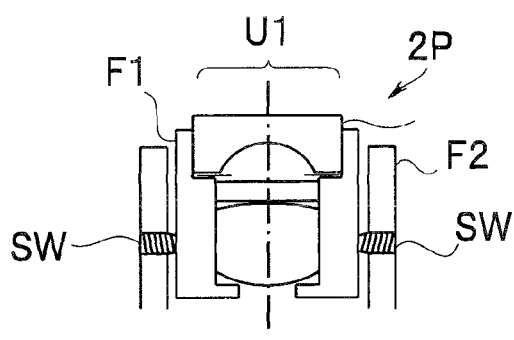
FIG. 52
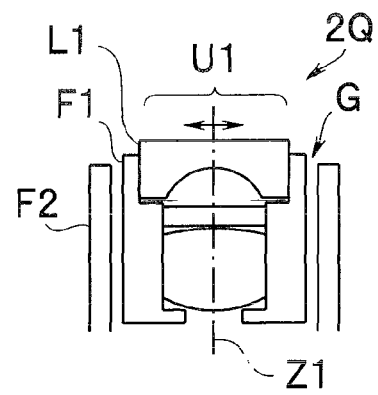

FIG. 72

| Example | d/f | d/IH | D1/f | D2/f | D1/D2 | \|f1\|/f | f2/f | G1f/f | G2f/f | G1f/G2f |
|---|---|---|---|---|---|---|---|---|---|---|
| 21 | 1.694 | 2.321 | 2.123 | 2.317 | 0.917 | 0.752 | 1.755 | 2.834 | 3.394 | 0.835 |
| 22 | 1.734 | 2.297 | 2.476 | 2.623 | 0.944 | 0.842 | 2.088 | 3.389 | 3.577 | 0.948 |
| 23 | 1.786 | 2.467 | 2.034 | 2.324 | 0.875 | 0.711 | 1.686 | 3.298 | 3.235 | 1.020 |
| 24 | 1.901 | 2.466 | 2.138 | 2.889 | 0.740 | 0.671 | 1.825 | 3.104 | 3.710 | 0.837 |

ENDOSCOPE FOR OBLIQUE VIEWING

This application claims benefit of Japanese Application No. 2008-240676 filed in Japan on Sep. 19, 2008, the contents of which are incorporated by this reference.

BACKGROUND OF THE INVENTION

1. Field of the Invention

The present invention relates to an endoscope for oblique viewing and, more particularly, to an endoscope for oblique viewing having a visual field direction converting element.

2. Description of the Related Art

Endoscopes include endoscopes for oblique viewing having a visual field direction different from the endoscope longitudinal direction (also referred to as "oblique-viewing endoscope" below, "endoscope" in single form denoting an oblique-viewing endoscope). Oblique-viewing endoscopes include a side-viewing endoscope having a visual field direction perpendicular to the endoscope longitudinal direction, a forward-oblique-viewing endoscope having a visual field direction inclined toward a distal end, and rearward-oblique-viewing endoscope having a visual field direction inclined toward a proximal end portion. An objective optical system (also referred to as "objective system" below) provided in a distal end portion of an oblique-viewing endoscope has a visual field direction converting element having a reflecting function/refractive function to convert the visual field direction from the endoscope longitudinal direction to a predetermined direction. For example, each of objective systems 102 of conventional oblique-viewing endoscopes shown in FIGS. 1 and 2 has a prism P disposed as a visual field direction converting element immediately after a negative first lens L1, which is a one-side flat lens having negative refractive power (Japanese Patent Application Laid-Open Publication Nos. 7-294806 and 2004-226722). Oblique-viewing objective systems are longer in entire length than straight-viewing objective systems, and the ray height at the front side of the prism P tends to be higher. Therefore the prism P and the first lens L1 tend to be larger in size. In the following description of objective systems, "front" designates the side closer to an object to be observed and "rear" designates the image pickup device side.

In some case, in a straight-viewing objective system 202, as shown in FIG. 3, optical filters FL1 and FL2 are disposed in the objective system (see, for example, Japanese Patent Application Laid-Open Publication No. 10-113329). In the oblique-viewing objective system 102, however, it is difficult to dispose an optical filter because a space for disposition of a visual field direction converting element is lost if an optical filter is disposed in the objective system. That is, if the lens distance is simply set larger, the entire length of the objective system 102 is increased and the outside diameter is also increased. Also, the configuration of the conventional straight-viewing objective system 202 having optical filters is not an optimum lens configuration for an oblique-viewing endoscope and, therefore, cannot be directly applied to the oblique-viewing endoscope objective system 102.

Also, there is a demand for incorporating a thicker forceps channel in an endoscope. Realizing this while preventing an increase in outside diameter of an endoscope requires reducing the size of the objective system and an illumination optical system (also referred to as "illumination system" below) 3 (see FIG. 7).

In some case of a rearward-oblique-viewing endoscope, an optical specification such as setting the oblique-viewing angle ($\theta 1$; see FIG. 14) indicating the center of the field of view to a large value of 15° or setting the field of view indicating the scope of the field of view to a large value of 100° or more is required to improve the treatment performance. The above-described specification, however, entails an increased possibility of occurrence of a cut-off of a portion of the field of view, i.e., an image cut-off, caused by intrusion of a nozzle 4, a distal end hood of the endoscope, a forceps rising base 6 or the like (see FIG. 12). Increasing the placement distance between the forceps rising base 6 and the objective system is effective in preventing the occurrence of an image cut-off. However, the size of the distal end portion is thereby increased to produce adverse effects in terms of insertability and operability. Therefore, achieving both the prevention of occurrence of a image cut-off and the prevention of an increase in size of a distal end portion 5 requires, in particular, reducing the ray height at the first lens L1 of the objective system 2 and reducing the lens diameter.

In the oblique-viewing endoscope objective system 102, as shown in FIG. 4, a substantially large frame thickness is required for securing the desired strength of a lens unit frame (lens frame) on the side of a charge coupled device (CCD) 20, which is an image pickup device at the rear of the prism P. Longitudinal sectional views referred to below are each a schematic sectional view taken parallel to or along the longitudinal direction or the optical axis of an endoscope, while perpendicular-to-longitudinal-direction sectional views are each a schematic sectional view taken along a direction perpendicular to the longitudinal direction or the like.

In the conventional image pickup system, the image pickup element and the objective system 102 are so large that there is no problem with the sizes of the lenses and the prism P even in designing the lens unit frame if the sizes of the lenses and the prism P are determined mainly on the basis of the relationship with the ray height. However, a reduction in diameter of the objective system is required for achieving a reduction in diameter of the endoscope while reducing the size of the image pickup device and increasing the number of pixels. However, if the diameter of the objective system is reduced, the desired strength of the lens unit frame cannot be secured. Since increasing the lens distance between the first lens L1 and the prism P is required in the lens unit frame design for the purpose of securing the designed strength of the lens unit frame, the sizes of the prism P and the first lens L1 are increased as a result of increasing the lens distance. The ray heights at the lens and the prism P are thereby increased, so that the possibility of an image cut-off by the forceps rising base 6 for example is increased.

It is also possible to dispose an objective system 102 in which a prism P is provided immediately before a CCD 20 of an oblique-viewing endoscope 101 to bend the optical axis, as shown in FIG. 5 (Japanese Patent Application Laid-Open Publication No. 8-76028) and to dispose a straight-viewing objective system 202 in an inclined state without using a prism P, as shown in FIGS. 6 and 7 (Japanese Patent Application Laid-Open Publication Nos. 2005-287851 and 5-113541). In the oblique-viewing endoscope, however, the entire length of the image pickup system including the objective system-image pickup device structure is long and, therefore, it is not easy to reduce the diameter of the distal end portion 5.

In FIG. 7, a light guide LG and an illumination lens CL in the form of a lens having negative refractive power, constituting an illumination system 3 described below, are also illustrated. In some position diagrams or the like to which references are made below, an objective system is represented by a first lens L1 alone and an illumination system 3 is represented by a lens having negative refractive power CL.

The diagrams not particularly specified are longitudinal sectional views in which a direction toward a distal end portion is indicated by an arrow (DE) and a direction toward a proximal end portion is indicated by an arrow (PE). Also, in some case, an illumination system and an objective system are collectively referred to as an optical system.

As described above, reducing the diameter of the distal end portion 5 requires a reduction in entire length of the objective system. An objective system having a reduced entire length is lower in optical performance and is incapable of securing a space for disposition of optical filters for color tone and image quality corrections, because the number of constituent lenses is small. Therefore, it is not easy to suitably design such an objective system in terms of optical performance with an image pickup device smaller in size and having an increased number of pixels.

Further, in an objective system of an oblique-viewing endoscope, since a prism P is provided, the possibility of occurrence of an angular deviation or the like is increased under the influence of variation in the optical path length or the angle of the prism P, and the influence of variation at the time of assembly on the lens unit frame as well as the influence of eccentricities of lenses. Therefore an oblique-viewing objective system needs optical adjustment of an angular deviation or the like at the time of assembly unlike a straight-viewing objective system.

In the lens configuration of an objective system ordinarily used in oblique-viewing endoscopes, a first lens L1, which is a negative lens, is disposed in front of the prism P, as described above. In this lens configuration, as shown in FIG. 9, a gap for adjustment is provided between a first lens L1 and a lens frame F holding the first lens L1, and a first lens L1 is moved in this gap in a direction perpendicular to an optical axis Z1 to make an optical adjustment of an angle of deviation or the like, i.e., an eccentricity adjustment.

After the optical adjustment, the gap for adjustment is filled with an adhesive to fix the first lens L1 in the lens frame F. However, there is a possibility of separation between the first lens L1 and the adhesive under the influence of heat in an external environment, the influence of a chemical solution at the time of sterilization of the endoscope, or the like. If separation occurs, moisture enters from the outside along the separated portions to cause dew condensation of water vapor on a lens inner surface and, hence, a fog on the lens inner surface such that an image to be observed is difficult to see. If the gap for adjustment is removed to avoid dew condensation, the objective system 2 varies largely in performance since optical adjustment cannot be made.

Reducing variations in performance of the objective system requires improving the accuracy of working on optical components including the lenses and the lens frame F, but mass production of high-accuracy component parts is not easy to perform. Also, it is difficult to perform the assembly process if no gap for adjustment is provided. Further, further improving the working accuracy is required for reducing variations of component parts having optical performances improved in correspondence with the reduction in size and the increase in number of pixels of image pickup devices. The first lens L1, which is a negative lens, is higher in refractive power than other lenses and is difficult to adjust finely.

Also, there is a possibility of considerable degradation in some other optical performance as a result of eccentricity adjustment to the first lens L1. In the case of an oblique-viewing objective system in particular, a partial defocus may be caused by an eccentricity adjustment made so that variation in the visual field direction is small and within a certain range in order to prevent the occurrence of an image cut-off. Conversely, if an adjustment is made to prevent a partial defocus, variation in the visual field direction becomes so large that the possibility of variation in the field of view and the possibility of occurrence of an image cut-off are increased.

Also, if the size of the first lens L1 in the objective system is increased, the distance between the objective system and the illumination system becomes so large that it is difficult for the illumination system to lightly and uniformly illuminate even a peripheral portion of the field of view for observation. At the time of closeup observation in particular, the illumination system cannot sufficiently illuminate in the field of view for observation; a peripheral portion of the field is left dark.

Further, in a case where the field of view for observation is made wider, that is, the field of view in the objective system is increased, for the purpose of improving observability, it is more difficult for the illumination system to sufficiently illuminate in the field of view and there is a possibility of a peripheral portion of the field of view for observation being dark.

The configuration of the distal end portion of the conventional oblique-viewing endoscope 101 is as shown in FIG. 7 or 8. A layout of optical component parts or the like in the distal end portion 5 for well balancedly illuminating in the entire scope of the field of view in a range of depth of field for observation is described, for example, in each of Japanese Patent Application Laid-Open Publication Nos. 2005-287851 and 5-113541.

In the conventional oblique-viewing endoscope 101 in which the illumination system 3 and the objective system 102 are disposed in this order from the distal end side DE, the entire region in the field of view cannot be well balancedly illuminated unless the illumination angle θ2 of the illumination system 3 is set equal to or larger than the oblique-viewing angle θ1 of the objective system 102, as shown in FIG. 10. At the time of closeup observation in particular, it is difficult to suitably perform illumination in a direction toward an upper region in the view (field of view) indicated by UP in FIG. 10. On the other hand, in the case of a disposition enabling suitable luminous intensity distribution at the time of closeup observation, it is difficult to suitably illuminate a lower portion of the view. Thus, the conventional oblique-viewing endoscope 101 may have a bad luminous intensity distribution such that a peripheral portion of the view is dark. Improving the luminous intensity distribution at the time of closeup observation requires reducing the distance between the objective system 102 and the illumination system 3. This is difficult to achieve because of the structure of the lens unit frame. In a case where the oblique-viewing angle θ1 is set to a large value of for example, 15° and in a case where the field of view for observation is increased to a larger field of view of 110° to 120°, it is further difficult to suitably illuminate the region in the field of view.

In the rearward-oblique-viewing endoscope in particular, the nozzle 4 and the forceps rising base 6 are disposed in the vicinity of the visual field direction and, therefore, the possibility of an image cut-off is increased due to the structure and the possibility is further increased if the oblique-viewing angle θ1 is increased or the angular scope of observation is increased.

SUMMARY OF THE INVENTION

An endoscope for oblique viewing includes an image pickup device, a front lens group having a positive refractive power, a visual field direction converting element disposed on the image pickup device side of the front lens group, and a rear lens group disposed on the image pickup device side of the visual field direction converting element and having a positive refractive power.

BRIEF DESCRIPTION OF THE DRAWINGS

FIGS. 18A to 18D are aberration diagrams of the objective system of the oblique-viewing endoscope in Embodiment 1;

FIG. 19 is a diagram showing a disposition in a case where Embodiment 1 is configured as a rearward-oblique-viewing optical system;

FIG. 20 is a diagram showing a disposition in a case where Embodiment 1 is configured as a forward-oblique-viewing optical system;

FIGS. 29A to 29D are aberration diagrams of the objective system of the oblique-viewing endoscope in Embodiment 5;

FIG. 30 is a diagram showing the optical configuration of an objective system of an oblique-viewing endoscope in Embodiment 6;

FIGS. 33A to 33D are aberration diagrams of the objective system of the oblique-viewing endoscope in Embodiment 7;

FIG. 34 is a diagram showing the optical configuration of an objective system of an oblique-viewing endoscope in Embodiment 8;

FIG. 38 is a diagram showing the optical configuration of an objective system of an oblique-viewing endoscope in Embodiment 9;

FIGS. 39A to 39D are aberration diagrams of the objective system of the oblique-viewing endoscope in Embodiment 9;

FIG. 42 is a diagram showing the optical configuration of an objective system of an oblique-viewing endoscope in Embodiment 11;

FIGS. 43A to 43D are aberration diagrams of the objective system of the oblique-viewing endoscope in Embodiment 11;

FIG. 48 is a table showing values of condition expressions in each embodiment;

FIG. 49 is a diagram showing a section of a structure taken along an optical axis, the structure integrally combining a front lens group;

FIG. 50 is a diagram showing a section of structure taken along an optical axis, the structure including a front lens group unit and a rear lens group unit integrally combining a visual field direction converting element and a rear lens group;

FIG. 51 is a diagram for explaining a method of fixing a front lens group unit and a rear lens group unit, showing a section of a structure taken along an optical axis;

FIG. 52 is a diagram for explaining shift adjustment of a front lens group unit with respect to a rear lens group unit, showing a section of a structure taken along an optical axis;

FIG. 72 is a table showing values of condition expressions in each embodiment.

DETAILED DESCRIPTION OF THE PREFERRED EMBODIMENTS

The operation and effects of the present invention will be described before descriptions of embodiments of the invention.

Figure 11:
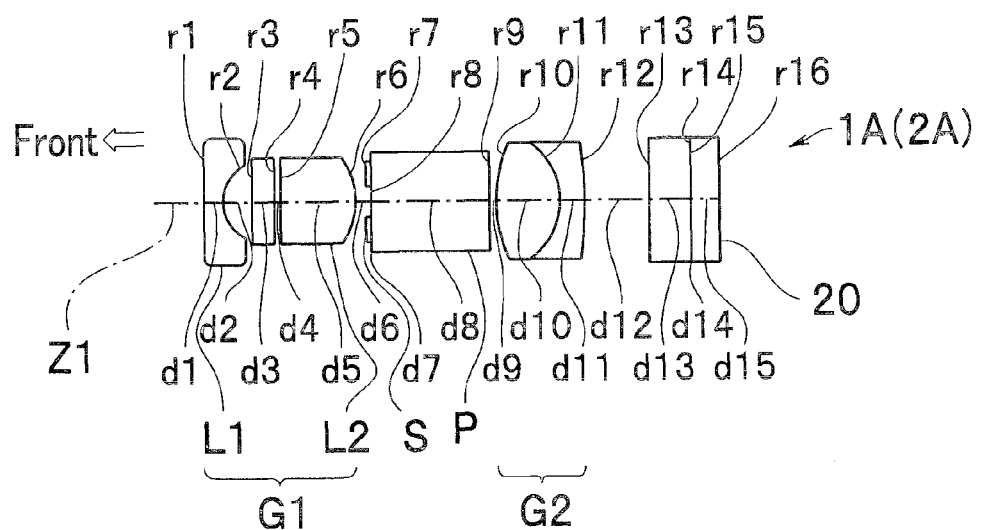
FIG. 11 is a diagram showing the optical configuration of an objective system of an oblique-viewing endoscope in Embodiment 1 of the present invention.

FIG. 11 shows an example of an objective optical system 2 of an oblique-viewing endoscope 1 according to the present invention. The objective system 2 includes a front lens group G1 having a positive refractive power, a prism P, which is a visual field direction converting element and a rear lens group G2 having a positive refractive power. The front lens group G1, the prism P and the rear lens group G2 are disposed in this order from an object 10 side (front side). In the objective system 2, the prism P is disposed between the front lens group G1 having a positive refractive power and the rear lens group G2 having a positive refractive power to enable setting longer the distance to lenses in front of the prism P. Therefore, the objective system 2 can have a lens frame having a sufficiently high strength even if the lenses are made small with reduction in size of a CCD 20 provided as an image pickup device. A mirror may be used as the visual field direction converting element. Each lens group may be constituted by one lens.

Further, a brightness stop (also referred to as "stop" below) S, disposed at the rear of the prism P (image pickup device side) in the conventional objective system, is disposed in front of the prism P in the objective system 2. In the objective system 2, therefore, the distance from the first lens L1 to the stop S can be reduced relative to that in the conventional objective system to reduce the ray height at the front lens group G1. As a result, the lens outside diameter can be reduced.

Further, the objective system 2 of the present invention is configured so as to satisfy the following condition expressions (1) and (2):

$$1.1 < d/f < 2.1 \tag{1}$$

$$1.4 < d/\mathrm{IH} < 3.0 \tag{2}$$

In these expressions, d represents the lens distance between the front lens group G1 and the rear lens group G2; f, the focal length of the entire system (entire objective optical system); and IH, the maximum image height. For example, in FIG. 11, $d = d6 + d7 + d8/n8 + d9$.

The above condition expressions (1) and (2) specify the lens distance between the front lens group G1 and the rear lens group G2 necessary for incorporating the prism P. The condition expression (1) relates to the focal length of the entire objective system 2, and the condition expression (2) relates to the image height. The lens distance d is shown in terms of air-converted length. As the refractive index of the medium, a numeric value with respect to e-line (wavelength 546.07 nm) is used.

If the ratio in each condition expression shown above is equal to or lower than the lower limit value, the visual field direction converting element having the size necessary for the objective system 2 cannot be disposed and the visual field direction converting element itself cannot be made. If the ratio in each condition expression is equal to or higher than the upper limit value, the distance between the front lens group G1 and the rear lens group G2 is so large that the entire objective system is considerably long; the diameter of each lens is large; and a distal end portion 5 is thick. Deviation beyond the upper limit is therefore undesirable.

The incidence-side size and the emergence-side size of the prism P, i.e., the dimensions of the external shape, are determined by the ray height of rays passing through the prism P and are, in ordinary cases, substantially equal to or smaller than the maximum image height. It is necessary that the necessary incidence-side and emergence-side sizes of the prism P when the optical axis is bent be secured. In actuality, the outside diameter of the prism P is set larger than the ray height with a margin by considering working and assembly variations or the like. The ray height in the objective system 2 varies with the focal length of the objective system 2 and the image height, and the necessary optical length of the prism P is thereby influenced. It is therefore preferable to satisfy the above condition expressions (1) and (2).

It is more preferable that the objective system 2 satisfy the following condition expressions (1A) and (2A) to be capable of further increasing the field of view and reducing the size of the image pickup device.

$$1.2 < d/f < 2.0 \tag{1A}$$

$$1.5 < d/\text{IH} < 2.7 \tag{2A}$$

In a case where the prism P is disposed in an intermediate section in the objective system 2 to bend the optical axis Z1 as in the present invention, the disposition of the prism P is important. In particular, the lens distance on the front side of the prism P largely influences the outside size of the prism P and the outside diameter of the distal end portion 5 and it is therefore necessary to optimize the lens distance. It is preferable to satisfy the following condition expressions (3) and (4) in order to optimize the lens distance.

$$1.4 < D1/f < 3.1 \tag{3}$$

$$2.0 < D2/f < 3.9 \tag{4}$$

In these expressions, D1 is the lens distance from the first lens surface in the objective system 2 to the object-side surface of the prism P; D2 is the lens distance from the image-side surface of the prism P to the image plane; and f is the focal length of the entire objective system 2. D1 and D2 are air-converted lengths.

The condition expressions (3) and (4) specify the lens distance on the front side of the prism P and the lens distance on the rear side of the prism P, respectively, and specify a configurational balance between the lens distances of the lens groups. If the ratio in condition expression (3) is equal to or lower than the lower limit value, the front lens group G1 and the lens unit frame cannot be made. If the ratio in condition expression (3) is equal to or higher than the upper limit value, the front lens group G1 becomes large, the objective system 2 is thereby made large, and the outside diameter of the endoscope is increased. If the ratio in condition expression (4) is equal to or lower than the lower limit value, the rear-side lens distance is short, the lens thickness is reduced, and working and assembly of the lenses are difficult. Further, a distance required for focus adjustment at the time of assembly is not provided. If the ratio in condition expression (4) is equal to or higher than the upper limit value, the rear lens group G2 is so long that the length of a rigid portion in the distal end portion 5 is considerably long and the operability of the endoscope 1 is low.

From consideration of capability of further increasing the field of view and reducing the size of the image pickup device, it is preferred that the objective system 2 satisfy the following condition expressions (3A) and (4A):

$$1.6 < D1/f < 2.8 \tag{3A}$$

$$2.3 < D2/f < 3.6 \tag{4A}$$

Further, it is preferred that the objective system 2 have, as a balance between the lens distances D1 and D2, a range shown by the following condition expression (5):

$$0.4 < D1/D2 < 1.0 \tag{5}$$

If the ratio in condition expression (5) is equal to or lower than the lower limit value, the lens distance of the front lens group G1 is so short that a lens unit frame having a sufficiently high strength cannot be made, although the size of the front lens group G1 can be reduced. If the ratio in condition expression (5) is equal to or higher than the upper limit value, the front lens group G1 is increased in size and the distal end portion 5 is thick.

The objective system 2 of the present invention has a positive lens group as the front lens group G1 and a positive lens group as the rear lens group G2, with the prism P provided as a visual field direction converting element therebetween. The positive lens group provided as the front lens group G1 includes a negative lens and a positive lens and therefore has a good refractive power distribution and is effective in correcting aberrations. In the objective system 2, since the front lens group G1 has a plurality of lenses, the lens distance on the front side of the prism P can be suitably increased and the number of lenses in the rear lens group G2 can be reduced. The stop S is disposed in the positive lens group provided as the front lens group G1, particularly at the rear of the front lens group G1 or between a negative lens provided as the first lens L1 constituting the front lens group G1 and a positive lens provided as the second lens L2 constituting the front lens group G1.

In the objective system 2 having the above-described dispositions, the lens distance of the front lens group G1 on the front side of the prism P is longer than that in the conventional objective system, but the distance from the first lens L1 in the first lens group G1 to the stop S is shorter than that in the conventional objective system in which the stop is disposed at the rear of the prism P. In the objective system 2, therefore, the outside diameters of the lenses at the rear of the prism P are smaller because the front lens group reduces the ray height, although the ray height is slightly increased at the lenses at the rear of the prism P. Since in the objective system 2 the lens outside diameter at the distal end side DE is reduced, the degree of freedom of disposition of the objective system 2 at the distal end portion 5 is increased. The objective system 2 is therefore capable of, for example, reducing an image cut-off caused by a forceps rising base 6 and reducing illumination unevenness at the time of closeup observation by reducing the distance between the disposed positions of the objective system 2 and an illumination system 3.

Configuring the rear lens group G2 of the objective system 2 by using a cemented lens formed by cementing a positive lens and a negative lens is effective in correcting a chromatic aberration.

It is also preferred that the front lens group G1 and the rear lens group G2 of the objective system 2 satisfy the following condition expressions (6) and (7):

$$1.5 < G1f/f < 6.0 \quad (6)$$

$$3.0 < G2f/f < 6.0 \quad (7)$$

In these expressions, G1f is the focal length of the front lens group G1, G2f is the focal length of the rear lens group G2, and f is the local length of the entire objective system 2.

The condition expressions (6) and (7) relate to refractive power configurations of the front lens group G1 and the rear lens group G2 disposed on opposite sides of the prism P having a large optical path length. The condition expression (6) relates to the front lens group G1, and the condition expression (7) relates to the rear lens group G2. If the ratio in condition expression (6) is equal to or lower than the lower limit value, the refractive power of the front lens group G1 is so strong that it is difficult to correct a spherical aberration, a coma and the like. Also, the back focal length is small and a sufficient amount of focus adjustment cannot be secured. If the ratio in condition expression (6) is equal to or higher than the upper limit value, the lens outside diameter of the front lens group G1 is large and the distal end portion 5 is thick. Also, the back focal length is so large that the entire objective system is considerably large in size. If the ratio in condition expression (7) is equal to or lower than the lower limit value, the refractive power of the rear lens group G2 is so strong that it is difficult to correct a spherical aberration, a coma and the like. Also, the back focal length is small and a sufficient amount of focus adjustment cannot be secured. If the ratio in condition expression (7) is equal to or higher than the upper limit value, the lens outside diameter of the rear lens group G2 and the back focal length are increased so that the entire objective system is considerably large in size.

In this case, it is further preferred that the objective system 2 satisfy the following condition expression (8):

$$0.3 < G1f/G2f < 2.0 \quad (8)$$

Condition expression (8) further specifies the refractive power distribution between the front lens group G1 and the rear lens group G2. If the ratio in condition expression (8) is equal to or lower than the lower limit value, the refractive power of the front lens group G1 is so strong that it is difficult to correct a spherical aberration, a coma and the like. Also, the back focal length is small and a sufficient amount of focus adjustment cannot be secured. If the ratio in condition expression (8) is equal to or higher than the upper limit value, the lens outside diameter of the front lens group G1 is large and the distal end portion 5 is thick. Also, the back focal length is so large that the entire objective system 2 is considerably large in size.

It is also preferred that the negative lens group and the positive lens group disposed in the front lens group G1 of the objective system 2 satisfy the following expressions (9) and (10):

$$0.5 < |f1|/f < 1.1 \quad (9)$$

$$1.3 < f2/f < 2.8 \quad (10)$$

In these expressions, f1 is the focal length of the negative lens group in the front lens group G1, f2 is the local length of the positive lens group in the front lens group G1, and f is the focal length of the entire objective system 2.

If the ratio in condition expression (9) is equal to or lower than the lower limit value, the refractive power of the negative lens group is so strong that it is difficult to correct aberrations. Further, the radius of curvature is small and the lens workability is low. If the ratio in condition expression (9) is equal to or higher than the upper limit value, the refractive power of the negative lens group is so weak that the lens outside diameter is considerably increased, the distances from the other lenses are increased, and the size of the endoscope 1 is thereby increased. If the ratio in condition expression (10) is equal to or lower than the lower limit value, the refractive power of the positive lens group is so strong that a spherical aberration and a coma are large. Also, the refractive power of each lens is strong and the workability of the lens is low. If the ratio in condition expression (10) is equal to or higher than the upper limit value, the refractive power of the positive lens group is so weak that the outside diameters of the visual field direction converting element and the rear lens group G2 are considerably large and the lens distance of the rear lens group G2 is considerably long, and the distal end portion 5 is thereby increased in size. Further, it is difficult to correct a spherical aberration and a coma.

From consideration of capability of further increasing the field of view and reducing the size of the image pickup device, it is further preferred that the objective system 2 satisfy the following condition expressions (9A) and (10A):

$$0.65 < |f1|/f < 1.0 \quad (9A)$$

$$1.5 < f2/f < 2.5 \quad (10A)$$

The objective system 2 of the endoscope 1 of the present invention is configured of a plurality of lens units each having optical elements such as lenses disposed in a lens frame, i.e., a first lens unit U1 and a second lens unit U2. The positions of the lens units can be changed relative to each other. The gap required for adjustment in the conventional objective system is not formed between the distal end lens (first lens L1) and the lens frame holding the distal-end lens. Therefore, moisture around the distal-end lens cannot easily penetrate to the lenses. Thus, the occurrence of a fog on the lenses can be prevented. Further, for eccentricity adjustment with respect to variations in the component parts including the prism and the lenses and assembly variations, a method in which one lens unit (first lens unit) formed of the positive front lens group disposed in front of the prism provided as a visual field direction converting element and the other lens unit (second lens unit) are made eccentric relative to each other is used in place of the conventional adjustment method to enable the optical adjustment to be easily performed.

In a case where the front lens group G1 of the objective system 2 is configured of a negative lens and a positive lens, each of the negative lens and the positive lens has a strong refractive power but these lenses are integrally made eccentric as the first lens unit to enable prevention of degradation in optical performance in contrast with individual eccentricity adjustment of one lens element. Further, in the objective system 2, the components including the stop S are grouped into lens units to be adjusted, that is, the objective system 2 is capable of simultaneously making eccentric the front lens group G1 particularly strong in refractive power in the objective system 2 and the stop S. In the objective system 2, therefore, the rotational symmetry of transmitted rays is not lost. Prevention of a reduction in optical performance is thus achieved. While unidimensional adjustment is illustrated in each diagram, three-dimensional adjustment is performed in actuality.

Figure 10:
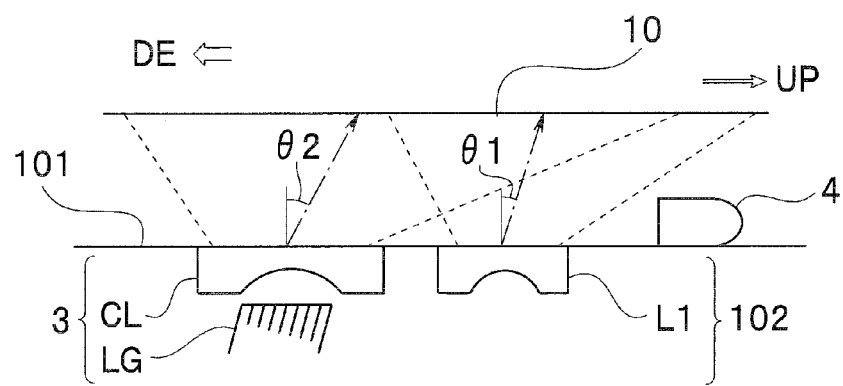
FIG. 10 is a diagram showing the relationship between the scope of the field of view of an objective system and the range of illumination of an illumination system of a conventional oblique-viewing endoscope.
Figure 12:
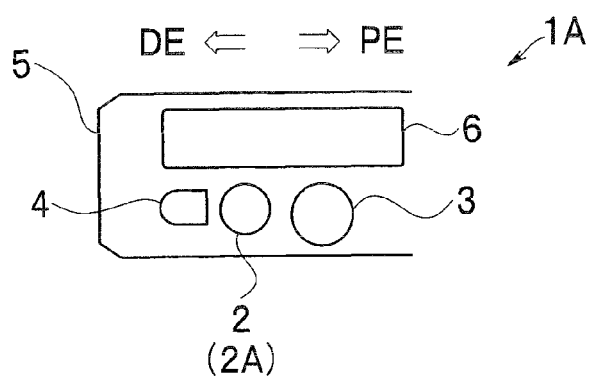
FIG. 12 is a schematic top view of a distal end portion of the oblique-viewing endoscope of the present invention.
Figure 13:
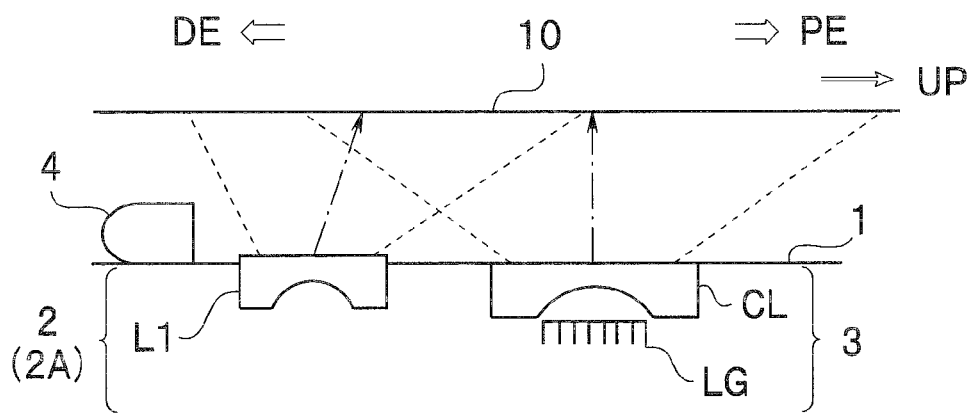
FIG. 13 is a diagram showing the relationship between the scope of the field of view of the objective system and the range of illumination of an illumination system in the oblique-viewing endoscope of the present invention.

Further, as shown in FIGS. 12 and 13, the distal end portion 5 of the oblique-viewing endoscope has a layout in which a nozzle 4, the objective system 2 and the illumination system 3 are disposed in this order from the distal end DE side. Therefore, in the case of the rearward-oblique-viewing endoscope in particular, the upper region in the view shown difficult to illuminate with the conventional endoscope as shown in FIG. 10 can be illuminated from a position in the upper side direction (UP) of the view, as shown in FIG. 13, thus evenly illuminating in the field of view for observation.

With the disposition made by attaching important to closeup observation, there is a possibility of deficiency of lightness at the lower side of the view because the objective system 2 and the illumination system 3 are disposed apart from each other. In such a case, the lightness in the view can be balanced by slightly shifting the direction of illumination with illumination light toward the objective system side.

If the nozzle 4 is disposed between the objective system 2 and the illumination system 3, the distance between the objective system 2 and the illumination system 3 is so large that illumination cannot be uniformly performed; a lightness non-uniformity occurs. From the viewpoint of preventing the occurrence of a lightness nonuniformity, it is preferred that the objective system 2 and the illumination system 3 be disposed close to each other, and that the nozzle 4 be disposed closer to the distal end relative to the objective system 2. Further, in the above-described disposition, a proximal portion of the forceps rising base 6 and the objective system 2 are at a certain distance from each other. Therefore, an image cut-off can be reduced. If the nozzle 4 is disposed on the illumination system 3 side, the nozzle 4 is remote from the objective system 2 side and, therefore, the function to clean the lens degrades. The nozzle 4 may be disposed laterally on the objective system 2, that is, along a top-bottom direction of FIG. 12. However, the outside diameter of the distal end portion 5 is increased in such a case. It is therefore preferable to dispose the nozzle 4 along the longitudinal direction.

Conditions for securing sufficient lightness even in a peripheral portion of the field of view in a range of depth of field for observation and preventing an image cut-off caused by the forceps rising base 6 or the like while enabling increasing the field of view of the objective system 2, reducing the diameter of the distal end portion 5 and increasing the diameter of the forceps channel, which conditions relate to the disposition of the distal end portion 5, will next be discussed.

Figure 14:
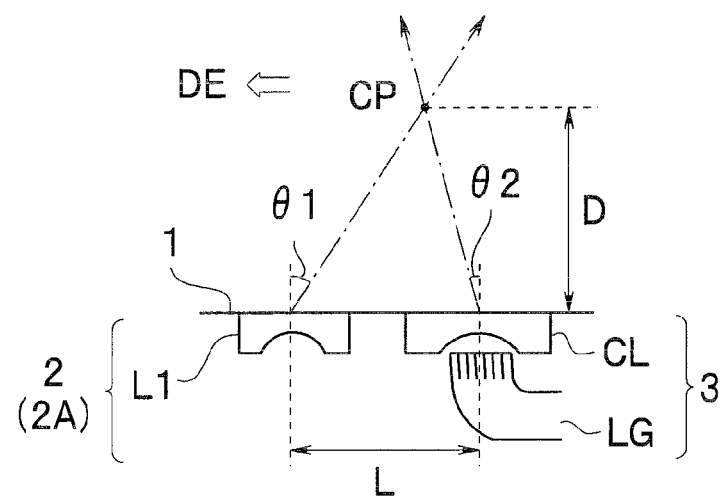
FIG. 14 is a diagram showing the relationship between the visual field direction of the objective system and the illumination direction of the illumination system in the oblique-viewing endoscope of the present invention.

In the endoscope 1, as shown in FIG. 14, the objective system 2 having the first lens L1 and the illumination system 3 having an illumination lens CL are disposed in this order from the distal end DE side. If the distance between a center (optical axis) of the objective system 2 and a center (optical axis) of the illumination system 3 is L; the oblique-viewing angle of the visual field direction of the objective system 2 (the angle between the optical axis and a direction perpendicular to the longitudinal direction of the endoscope) is $\theta 1$; the angle of the direction of illumination from the illumination system 3 (the angle between the optical axis of rays emitted from a center of a light emitting member such as an light guide (LG) bundle or a light emitting diode (LED) and transmitted through the illumination optical system and a direction perpendicular to the longitudinal direction of the endoscope) is $\theta 2$; the point of intersection of the visual field direction (optical axis) of the objective system 2 and the illumination direction (optical axis) of the illumination system 3 is CP; and the distance between the first surface of the objective system 2 (illumination system 3) and the point of intersection CP is D, the relationship shown by the following expression (11) is established.

$$L = D(\tan \theta 1 + \tan \theta 2) \tag{11}$$

Accordingly, the illumination angle $\theta 2$ of the illumination system 3 is $\theta 2 = \tan^{-1}(L/D - \tan \theta 1)$.

The visual field direction of the objective system 2 is directed toward the illumination system 3, and the illumination direction of the illumination system 3 is directed toward the objective system 2. If the illumination direction of the illumination system 3 is set so as to illuminate a space along the visual field direction of the objective system 2, illumination can be performed so that the lightness in the observed view is uniform. If the distance D is set to the best position in the objective system 2, the lightness can be balanced through the entire range from the near point to the far point in the depth of field. Reducing the distance L is preferable for reducing the influence of a parallax at the time of closeup observation. However, the distance L cannot be reduced to a value equal to or smaller the lens outside diameter of any of the objective system 2 and the illumination system 3. The lens configuration of the present invention is effective in reducing the distance L because of its capability of achieving a reduction in size of the first lens unit L1 in particular. As a result, the objective system 2 of the present invention can be disposed with a range of 3 mm≤L≤5 mm even in the case of using the visual field direction converting element.

Figure 15:
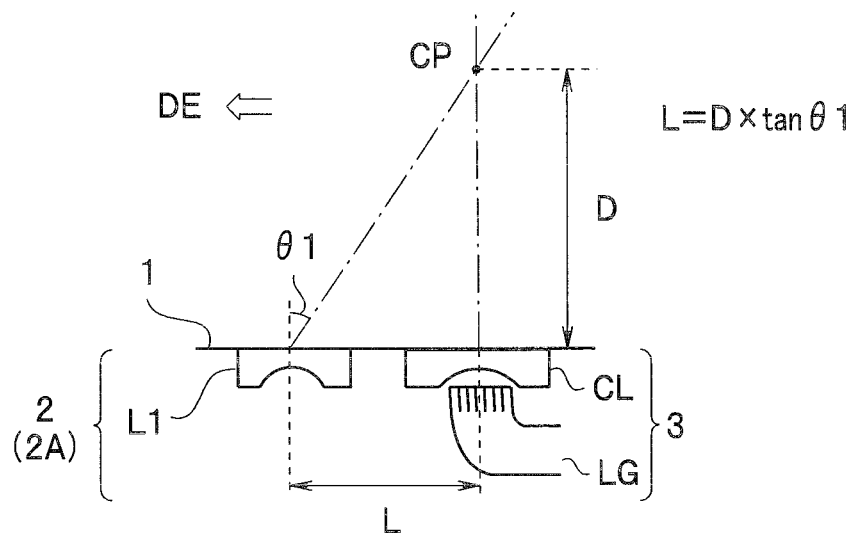
FIG. 15 is a diagram showing the relationship between the visual field direction of the objective system and the illumination direction of the illumination system in the oblique-viewing endoscope of the present invention.

In the case of an endoscope 1 not used for closeup observation, there is no lightness balance problem in practice even when the illumination direction of the illumination system 3 is perpendicular to the longitudinal direction of the endoscope, that is $\theta 2=0$ (see FIG. 15). In this case, the above expression (11) is as shown by the following expression (12):

$$L = D \tan \theta 1 \tag{12}$$

Accordingly, the relationship between the oblique-viewing angle $\theta 1$, the distance L and the distance D is as shown by the following expression (13):

$$\theta 1 = \tan^{-1}(L/D) \tag{13}$$

In a case where L=4 mm and D=15 mm, if the oblique-viewing angle $\theta 1$ is in the range not exceeding 14.9°, a lightness balance can be obtained with no problem. However, when the oblique-viewing angle $\theta 1$ is in this range, it is difficult to uniformly illuminate in the field of view for observation. It is therefore preferable to direct the illumination direction toward the objective system 2. In ordinary cases, the distribution range of the illumination system 3 is so wide that the influence of a parallax due to the distance between the objective system 2 and the illumination system 3 is negligible if the distal end portion 5 is not brought close to the object 10 by setting the distance to the object 10 to 5 mm or less. In the case of ordinary observation, therefore, there is no problem with setting the visual field direction of the objective system 2 and the illumination direction of the illumination system 3 substantially the same.

The magnitude of the oblique-viewing angle $\theta 1$ of the visual field direction is within a range shown by the following expression (14):

$$0° \leq \theta 1 \leq 20° \tag{14}$$

A case where $\theta 1=0$ corresponds to a side-viewing objective system of a side-viewing endoscope.

If the distance D is set in the vicinity of the best distance in the objective system 2, generally uniform image lightness, i.e., a lightness balance with no problem can be obtained. It is therefore preferred that the distance D be within a range shown by following expression (15):

$$10 \text{ mm} \leq D \leq 20 \text{ mm} \tag{15}$$

However, it is further preferred that if importance is attached to closeup observation the distance D be set within a range: 5 mm≤D≤15 mm. Preferably, in this case, the illumination angle θ2 of the illumination system 3 is set within a range: 0°≤θ2≤25°, depending on observation circumstances.

In the case of the oblique-viewing objective system, if the distal end lens (first lens) is formed into an asymmetric shape, e.g., a wedge shape to produce the oblique-viewing angle θ1, the balance in the top-bottom direction of the view in the scope of observation is changed to such an extent that it is difficult to uniformly illuminate along the top-bottom direction of the view. It is therefore preferred that the lens should not be asymmetric except a case where oblique-viewing angle θ1 is small, for example, 5°.

Figure 1:
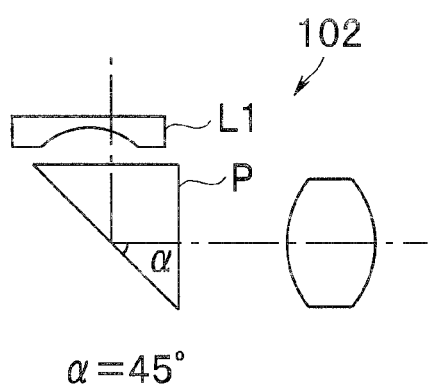
FIG. 1 is a diagram showing the optical configuration of an objective system of a conventional oblique-viewing endoscope.
Figure 2:
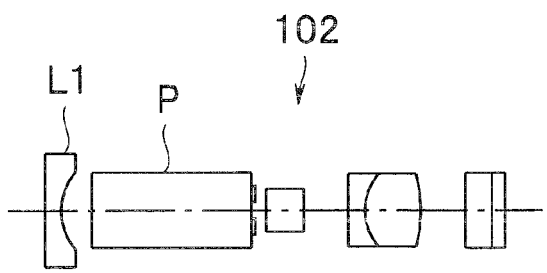
FIG. 2 is a diagram showing the optical configuration of an objective system of a conventional oblique-viewing endoscope.
Figure 3:
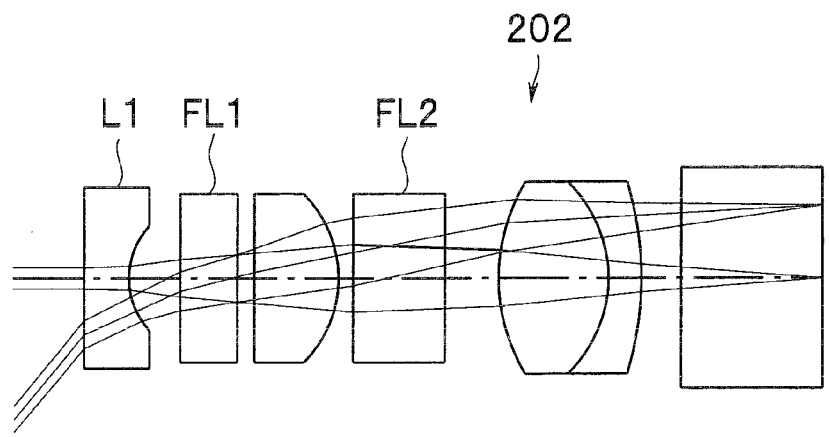
FIG. 3 is a diagram showing the optical configuration of a straight-viewing objective system of a conventional endoscope.
Figure 4:
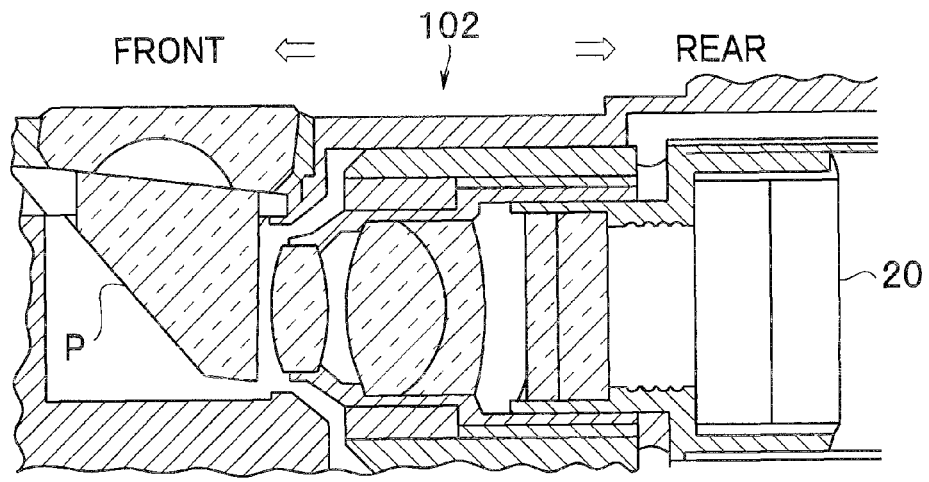
FIG. 4 is a longitudinal sectional view of an example of a structure of an objective system of a conventional side-viewing endoscope.
Figure 5:
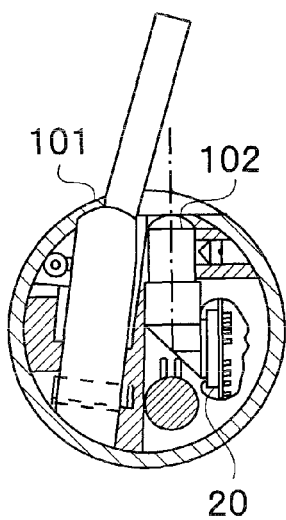
FIG. 5 is a perpendicular-to-longitudinal-direction sectional view of an objective system of a conventional side-viewing endoscope in which a prism is disposed immediately before an image pickup device to bend the optical axis.
Figure 6:
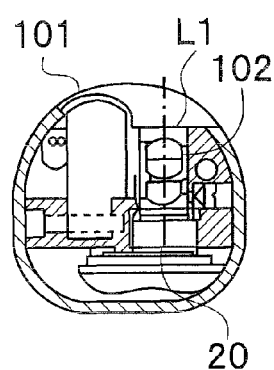
FIG. 6 is a perpendicular-to-longitudinal-direction sectional view of conventional side-viewing endoscope in which a straight-viewing objective system is slantingly disposed.
Figure 7:
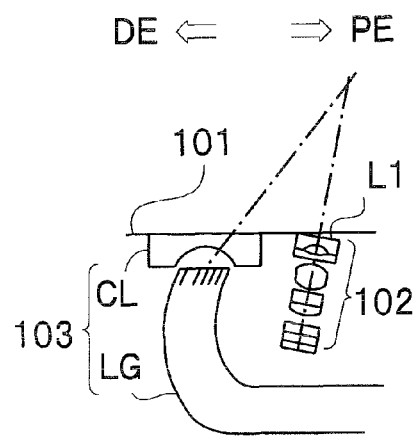
FIG. 7 is a diagram showing a disposition of an objective system and an illumination system of a conventional endoscope.
Figure 8:
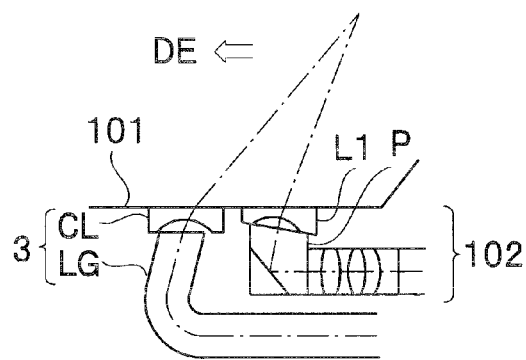
FIG. 8 is a diagram showing a disposition of an objective system and an illumination system of a conventional endoscope.
Figure 9:
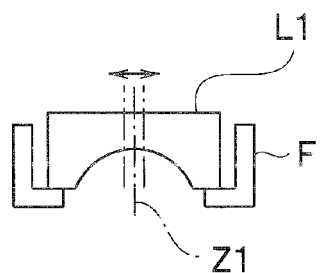
FIG. 9 is a diagram showing optical adjustment in a lens frame of a first lens of an objective system in a conventional endoscope.
Figure 16:
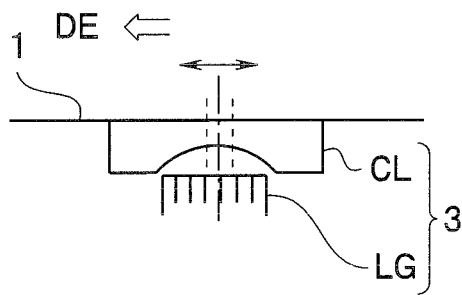
FIG. 16 is a diagram showing shifting of an illumination lens with respect to an illumination light source such as a light guide.
Figure 17:
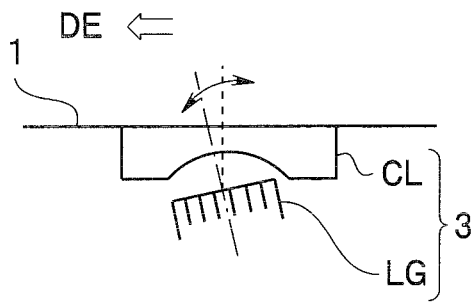
FIG. 17 is a diagram showing tilting of an illumination lens with respect to an illumination light source such as a light guide.

As a method of setting the illumination angle θ2 of the illumination system 3 to an angle other than 0°, a method of making the illumination lens CL eccentric, that is, shifting the lens (see FIG. 16) and a method of making an illumination light source such as a light guide eccentric, that is, tilting the light source (see FIG. 7) are conceivable. Adjustment of the amount of tilt and the amount of shift may be enabled. In a case where the illumination system 3 has a light guide LG, the illumination angle θ2 can be set by slantingly cutting a distal end portion of the light guide LG, as shown with respect to the conventional art (FIG. 10).

Also in a case where a light emitting device such as a light emitting diode (LED) is used as an illumination light source, the illumination angle θ2 can be changed through eccentricity adjustment of the illumination lens CL or the light emitting device.

In the objective system 2 of the present invention, an optical filter can be easily disposed.

Embodiments of the objective system 2 of the oblique-viewing endoscope 1 according to the present invention will be described. In some cases, in the following description, reference characters indicating components are discriminated by adding one alphabetic letter as a suffix to each character.

Embodiment 1

As shown in FIG. 11, an objective system 2A of an oblique-viewing endoscope 1A in Embodiment 1 has a positive front lens group G1, a positive rear lens group G2, a prism P interposed between the front and rear lens groups as a visual field direction converting element, and a stop S provided between the front lens group G1 and the prism P. In FIG. 11 and other sectional views each taken along the optical axis of an objective system and showing the configuration of the objective system, reference character r denotes a curved surface of a component reference character d denotes the distance between surfaces on the optical axis (the thickness of each optical member and the air distance); and the optical axis Z1 is shown in straight line form.

That is, in the objective system 2A, the front lens group G1 constituted by a first lens L1 having a negative refractive power and a second lens L2 having a positive refractive power is disposed in front of the prism P (at the left side of the figure) and the second lens group G2 constituted by a cemented lens and having a positive refractive power is disposed at the rear of the prism P (at the right side of the figure). The second lens group G2 is constituted by a cemented lens formed by cementing together a positive lens and a negative lens.

The stop S is disposed on the front side of the prism P to lower the ray height at the front lens group G1 and reduce the lens outside diameter. Therefore the first lens L1 has a reduced diameter. Also, since the objective system 2A has a negative lens and a positive lens disposed in front of the stop S, the refractive power of the front lens group G1 can be easily balanced, so that aberrations such as a spherical aberration and a coma are small.

Numeric data and other data on the optical members constituting the optical system of Embodiment 1 are shown below. In the numeric data, r denotes the radius of curvature of each surface; d, the thickness or the air distance of each optical member; n(e), the refractive index of each optical member with respect to e-line; ν(e), the Abbe constant of each optical member with respect to e-line; f, the focal length of the entire objective system 2A; IH, the image height; W, the half field of view; G1f, the focal length of the front lens group G1; and G2f, the focal length of the rear lens group G2. The unit r and d is mm, and f is standardized to 1 mm.

These symbols are used in common in numeric data on other embodiments described below.

The numeric data on Embodiment 1 is shown below.

| Surface No. | r | d | n(e) | ν(e) |
|---|---|---|---|---|
| 1 | ∞ | 0.3705 | 1.88814 | 40.53 |
| 2 | 0.6910 | 0.5309 | 1. | |
| 3 | ∞ | 0.3828 | 1.51564 | 74.74 |
| 4 | ∞ | 0.1030 | 1. | |
| 5 | ∞ | 1.3585 | 1.75844 | 52.08 |
| 6 | −1.4841 | 0.2452 | 1. | |
| 7(Stop) | ∞ | 0.0370 | 1. | |
| 8 | ∞ | 2.1612 | 1.88815 | 40.52 |
| 9 | ∞ | 0.0988 | 1. | |
| 10 | 3.2326 | 1.1431 | 1.75844 | 52.08 |
| 11 | −1.2185 | 0.4322 | 1.85504 | 23.59 |
| 12 | −7.0932 | 1.1081 | 1. | |
| 13 | ∞ | 0.7410 | 1.51825 | 63.94 |
| 14 | ∞ | 0.0123 | 1.52233 | 52.71 |
| 15 | ∞ | 0.4940 | 1.50700 | 63.00 |
| 16 | ∞ | | | | f = 1, IH = 0.783, W = 49.585°
d/f = 1.526
d/IH = 1.949
D1/f = 2.138
D2/f = 2.914
D1/D2 = 0.734
|f1|/f = 0.778
f2/f = 1.957
G1f/f = 3.170
G2f/f = 3.775
G1f/G2f = 0.840

FIGS. 18A to 18D are aberration diagrams of the objective system 2A of the present embodiment. FIG. 18A shows spherical aberrations. The middle two aberration diagrams (FIGS. 18B and 18C) each show ΔS (sagittal) and ΔS (meridional) with respect to the reference wavelength in e-line. FIGS. 18B and 18C show ΔS with a solid line and ΔM with a broken line. FIG. 18D shows a distortion. In FIG. 18A, the value of the F number (FNO) is shown. In FIGS. 18B and 18D, the field of view (2ω) is shown. The unit of the spherical aberrations, commas and astigmatisms on the abscissa is mm, and the unit of the distortion on the abscissa is %. Symbols (A) to (E) denote measurement wavelengths, (A) for 656.27 nm: C-line, (B) for 587.56 nm: d-line, (C) for 546.07 nm: e-line, (D) for 486.13 nm: F-line, (E) for 435.83 nm: g-line. The same apply in other aberration diagrams shown below.

FIG. 19 shows a concrete example of the disposition of an objective system 2A1 of a rearward-oblique-viewing optical system having a prism PA1 for a rearward viewing angle of 15° according to the present embodiment. FIG. 20 shows a concrete example of the disposition of an objective system 2A2 of a forward-oblique-viewing optical system having a prism PA2 for a forward viewing angle of 45° according to the present embodiment.

Embodiment 2

Figure 21:
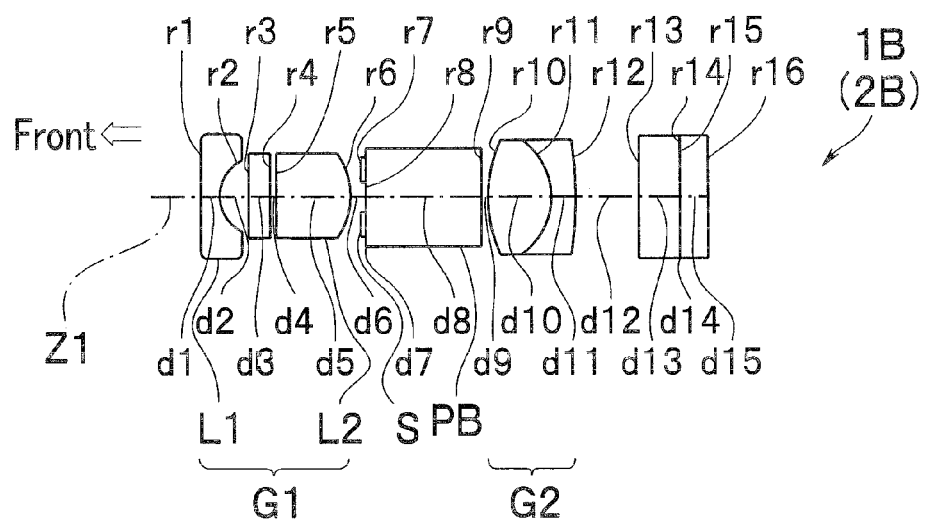
FIG. 21 is a diagram showing the optical configuration of an objective system of an oblique-viewing endoscope in Embodiment 2.
Figure 22A:
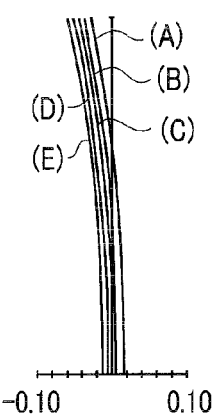
FIGS. 22A to 22D are aberration diagrams of the objective system of the oblique-viewing endoscope in Embodiment 2.
Figure 22B:
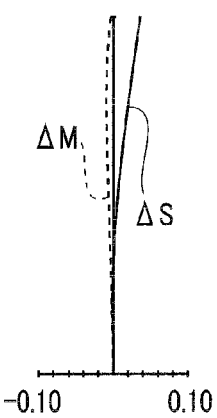
Figure 22C:
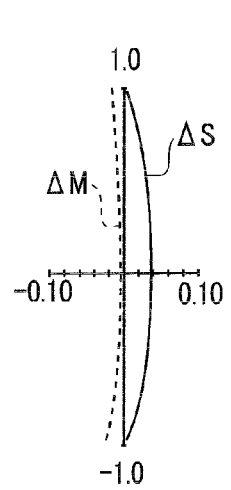
Figure 22D:
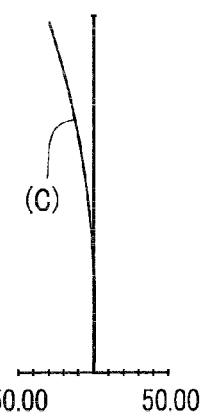

FIG. 21 shows the configuration of an objective system 2B of an oblique-viewing endoscope 1B in Embodiment 2. The configuration of the objective system 2B in the present embodiment is similar to that of the objective system 2A in Embodiment 1. The same reference characters are used for the same components as those in Embodiment 1, and the description for the same components will not be repeated. In the objective system 2B in the present embodiment, a high-refraction material having a refractive index of about 2.1 or more is used as the material of a prism PB which is a visual field direction converting element. Because of the use of the high-refraction material, the air-converted length of the prism PB is short and the substantial space for disposition of the prism PB is small. FIGS. 22A to 22D are aberration diagrams of the objective system 2B in the present embodiment.

Numeric data on Embodiment 2 is shown below.

| Surface No. | r | d | n(e) | ν(e) |
|---|---|---|---|---|
| 1 | ∞ | 0.3716 | 1.88814 | 40.53 |
| 2 | 0.7025 | 0.5326 | 1. | |
| 3 | ∞ | 0.3840 | 1.51564 | 74.74 |
| 4 | ∞ | 0.1641 | 1. | |
| 5 | 15.9787 | 1.3625 | 1.75844 | 52.08 |
| 6 | −1.5099 | 0.1858 | 1. | |
| 7(Stop) | ∞ | 0.0372 | 1. | |
| 8 | ∞ | 2.1675 | 2.19048 | 32.77 |
| 9 | ∞ | 0.1261 | 1. | |
| 10 | 3.4178 | 1.1310 | 1.75844 | 52.08 |
| 11 | −1.2825 | 0.3512 | 1.85504 | 23.59 |
| 12 | −8.5328 | 1.0351 | 1. | |
| 13 | ∞ | 0.7432 | 1.51825 | 63.94 |
| 14 | ∞ | 0.0124 | 1.52233 | 52.71 |
| 15 | ∞ | 0.4954 | 1.50700 | 63.00 |
| 16 | ∞ | | | |

F = 1, IH = 0.785, W = 49.601°
d/f = 1.338
d/IH = 1.704
D1/f = 2.145
D2/f = 2.820
D1/D2 = 0.761
|f1|/f = 0.791
f2/f = 1.882
G1f/f = 2.517
G2f/f = 4.162
G1f/G2f = 0.605

Embodiment 3

Figure 23:
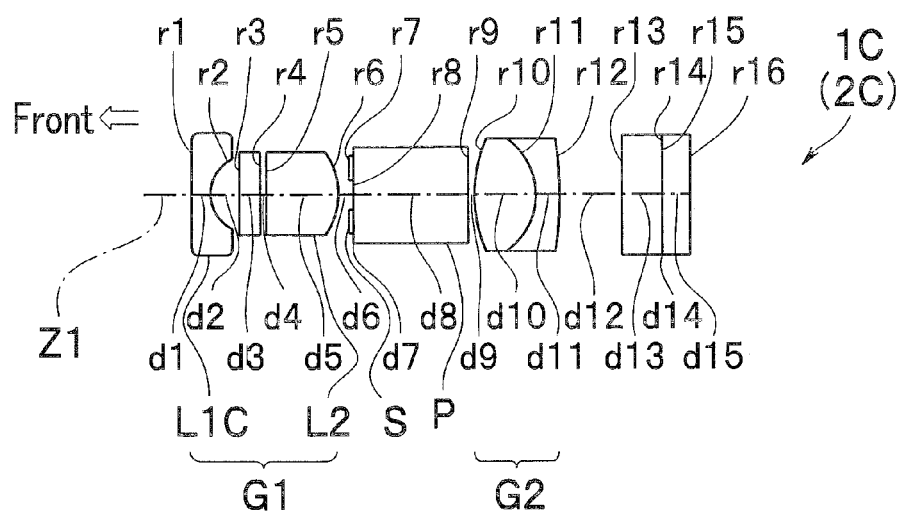
FIG. 23 is a diagram showing the optical configuration of an objective system of an oblique-viewing endoscope in Embodiment 3.
Figure 24A:
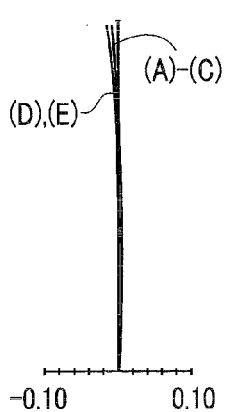
FIGS. 24A to 24D are aberration diagrams of the objective system of the oblique-viewing endoscope in Embodiment 3.
Figure 24B:
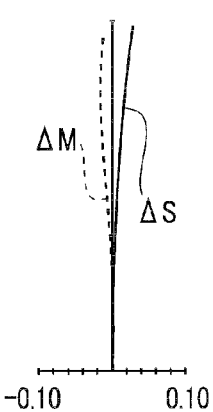
Figure 24C:
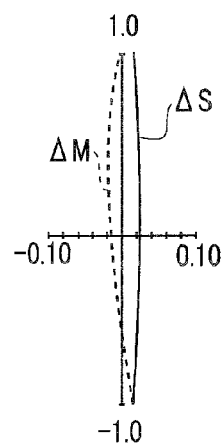
Figure 24D:
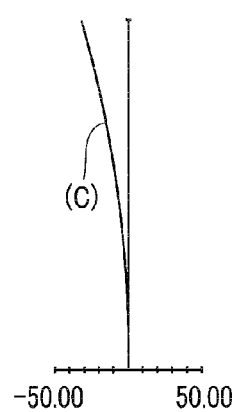

FIG. 23 shows the optical configuration of an objective system 2C of an oblique-viewing endoscope 1C in Embodiment 3. The configuration in the present embodiment is similar to that of the objective system 2A in Embodiment 1. The same reference characters are used for the same components as those in Embodiment 1, and the description for the same components will not be repeated. In the present embodiment, a first lens L1C is formed of a sapphire crystal material. The refractive index of sapphire is rather low but use of sapphire is advantageous in that the hardness of sapphire is high and the lens outer surface is resistant to scratch or the like. In an endoscope using a lens having a small outside diameter of several millimeters in particular, even a small scratch may badly influence the image quality by causing image nonuniformity or a flare for example. In the oblique-viewing endoscope 1C using the high-hardness material, however, such band influence cannot occur easily. FIGS. 24A to 24D are aberration diagrams of the objective system 2C in the present embodiment.

Numeric data on Embodiment 3 is shown below.

| Surface No. | r | d | n(e) | ν(e) |
|---|---|---|---|---|
| 1 | ∞ | 0.3641 | 1.77077 | 72.04 |
| 2 | 0.6675 | 0.5218 | 1. | |
| 3 | ∞ | 0.3762 | 1.51564 | 74.74 |
| 4 | ∞ | 0.0607 | 1. | |
| 5 | ∞ | 1.3349 | 1.59143 | 60.88 |
| 6 | −1.2954 | 0.2157 | 1. | |
| 7(Stop) | ∞ | 0.0364 | 1. | |
| 8 | ∞ | 2.1237 | 1.88815 | 40.52 |
| 9 | ∞ | 0.0971 | 1. | |
| 10 | 2.6636 | 1.1205 | 1.75844 | 52.08 |
| 11 | −1.1386 | 0.4717 | 1.85504 | 23.59 |
| 12 | −6.7746 | 1.1286 | 1. | |
| 13 | ∞ | 0.7281 | 1.51825 | 63.94 |
| 14 | ∞ | 0.0121 | 1.52233 | 52.71 |
| 15 | ∞ | 0.4854 | 1.50700 | 63.00 |
| 16 | ∞ | | | | f = 1, IH = 0.769, W = 49.084°
d/f = 1.474
d/IH = 1.917
D1/f = 2.127
D2/f = 2.927
D1/D2 = 0.727
|f1|/f = 0.866
f2/f = 2.190
G1f/f = 5.494
G2f/f = 3.208
G1f/G2f = 1.712

Embodiment 4

Figure 25:
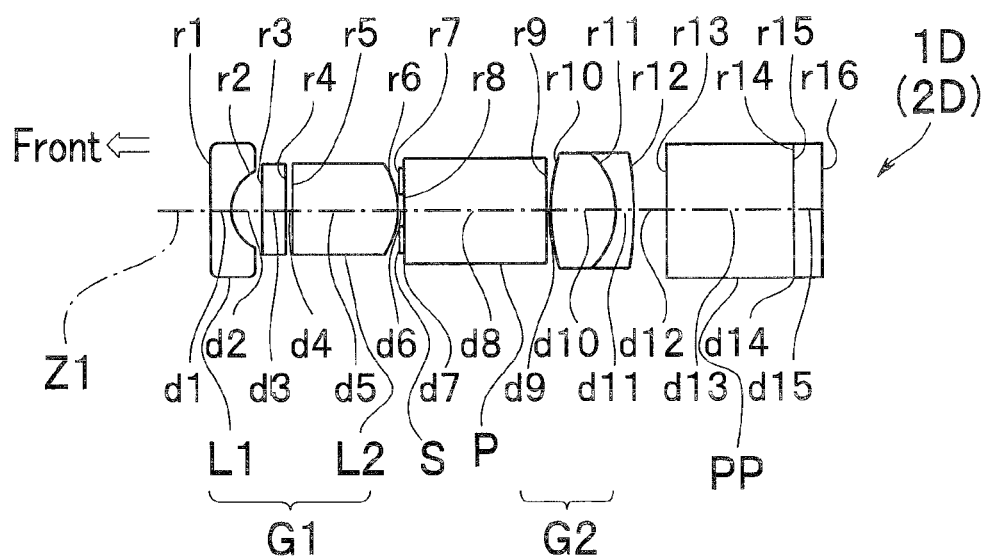
FIG. 25 is a diagram showing the optical configuration of an objective system of an oblique-viewing endoscope in Embodiment 4.
Figure 26:
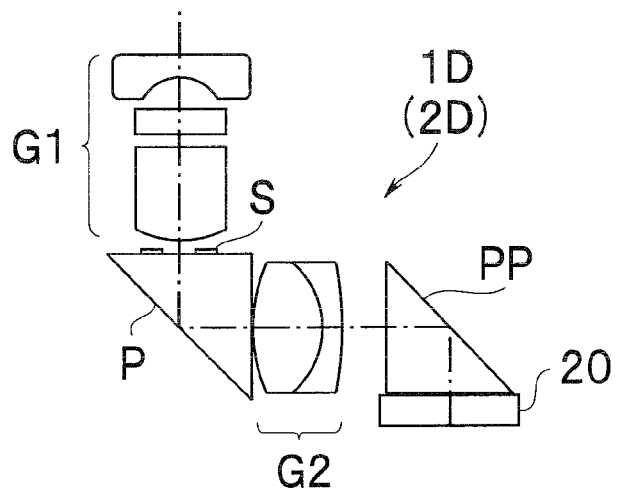
FIG. 26 is a diagram showing a concrete disposition in the objective system of the oblique-viewing endoscope in Embodiment 4.
Figure 27A:
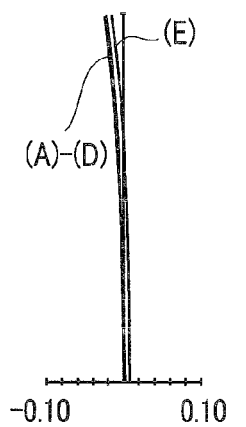
FIGS. 27A to 27D are aberration diagrams of the objective system of the oblique-viewing endoscope in Embodiment 4.
Figure 27B:
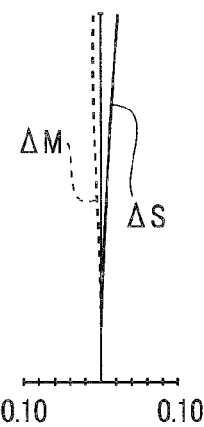
Figure 27C:
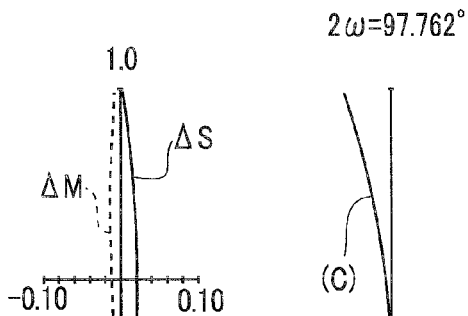
Figure 27D:
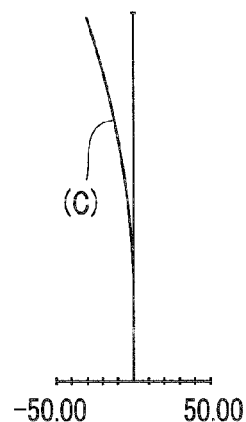

FIG. 25 shows the optical configuration of an objective system 2D of an oblique-viewing endoscope 1D in Embodiment 4. The basic configuration of the objective system 2D in the present embodiment is similar to that of the objective system 2A in Embodiment 1. The same reference characters are used for the same components as those in Embodiment 1, and the description for the same components will not be repeated. The objective system 2D in the present embodiment also has a prism PP having a large optical path length immediately before the image pickup device. More specifically, the objective system 2D is configured as shown in FIG. 26. This configuration is effective in a case where the image pickup device is large and it is difficult to dispose the image pickup device perpendicularly to the longitudinal direction of the endoscope, and where there is a need to provided a space (at the right-hand side of FIG. 26) in the distal end portion 5, for example, for a reason relating to the disposition of a light guide LG. FIGS. 27A to 27D are aberration diagrams of the objective system 2D in the present embodiment.

Numeric data on Embodiment 4 is shown below.

| Surface No. | r | d | n(e) | ν(e) |
|---|---|---|---|---|
| 1 | ∞ | 0.3696 | 1.88814 | 40.53 |
| 2 | 0.7874 | 0.5298 | 1. | |
| 3 | ∞ | 0.3819 | 1.51564 | 74.74 |
| 4 | ∞ | 0.1848 | 1. | |
| 5 | ∞ | 1.4783 | 1.75844 | 52.08 |
| 6 | −1.6703 | 0.0616 | 1. | |

-continued

| Surface No. | r | d | n(e) | ν(e) |
|---|---|---|---|---|
| 7(Stop) | ∞ | 0.0370 | 1. | |
| 8 | ∞ | 2.3408 | 1.88815 | 40.52 |
| 9 | ∞ | 0.0740 | 1. | |
| 10 | 4.9517 | 1.0472 | 1.75844 | 52.08 |
| 11 | −1.1284 | 0.3080 | 1.85504 | 23.59 |
| 12 | −3.5450 | 0.5914 | 1. | |
| 13 | ∞ | 2.0943 | 1.51825 | 63.93 |
| 14 | ∞ | 0.0123 | 1.52233 | 52.71 |
| 15 | ∞ | 0.4928 | 1.50700 | 63.00 |
| 16 | ∞ | | | | f = 1, IH = 0.781, W = 48.881°
d/f = 1.412
d/IH = 1.808
D1/f = 2.102
D2/f = 3.141
D1/D2 = 0.669
|f1|/f = 0.887
f2/f = 2.202
G1f/f = 3.973
G2f/f = 3.430
G1f/G2f = 1.158

Embodiment 5

Figure 28:
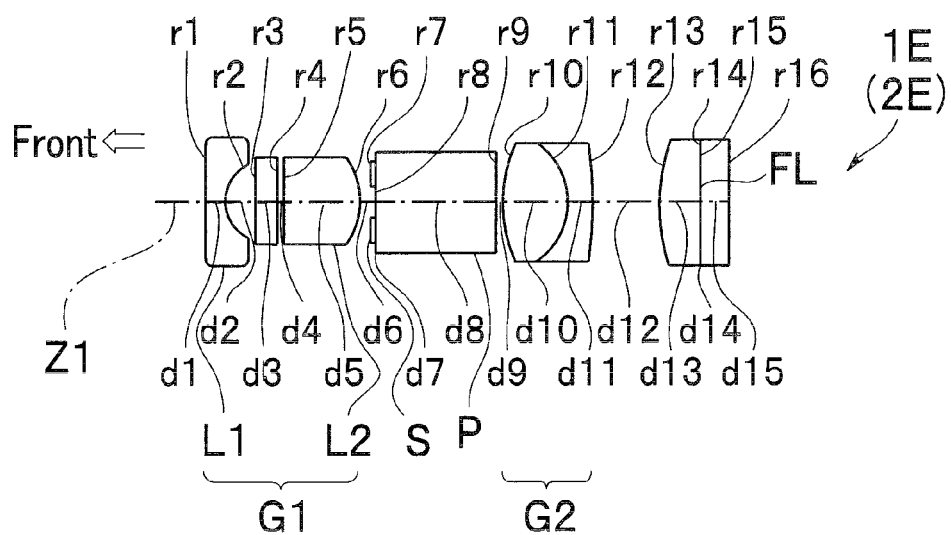
FIG. 28 is a diagram showing the optical configuration of an objective system of an oblique-viewing endoscope in Embodiment 5.
Figure 31A:
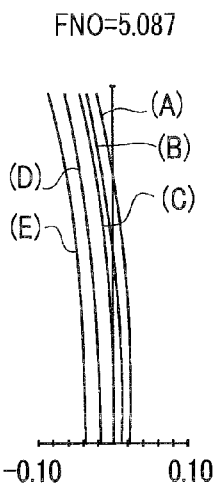
FIGS. 31A to 31D are aberration diagrams of the objective system of the oblique-viewing endoscope in Embodiment 6.
Figure 31B:
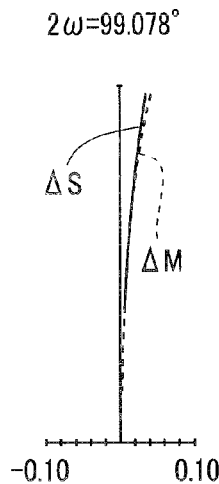
Figure 31C:
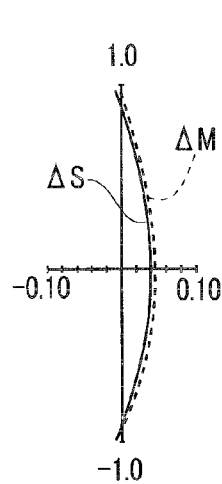
Figure 31D:
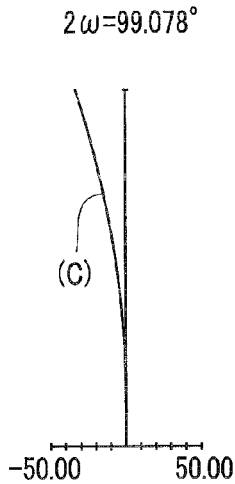

FIG. 28 shows the optical configuration of an objective system 2E of an oblique-viewing endoscope 1E in Embodiment 5, The basic configuration of the objective system 2E in the present embodiment is similar to that of the objective system 2A in Embodiment 1. The same reference characters are used for the same components as those in Embodiment 1, and the description for the same components will not be repeated. In the present embodiment, a field lens FL formed of a flat lens having positive refractive power is disposed immediately before the image pickup device. In particular, in a case where a characteristic of incidence of rays on the light receiving portion of the device is specified as a characteristic of the image pickup device, this configuration is effective in setting the desired ray incidence angle. FIGS. 29A to 29D are aberration diagrams of the objective system 2E in the present embodiment.

Numeric data on Embodiment 5 is shown below.

| Surface No. | r | d | n(e) | ν(e) |
|---|---|---|---|---|
| 1 | ∞ | 0.3711 | 1.88814 | 40.53 |
| 2 | 0.7245 | 0.5318 | 1. | |
| 3 | ∞ | 0.3834 | 1.51564 | 74.74 |
| 4 | ∞ | 0.1713 | 1. | |
| 5 | ∞ | 1.3606 | 1.75844 | 52.08 |
| 6 | −1.5452 | 0.1855 | 1. | |
| 7(Stop) | ∞ | 0.0371 | 1. | |
| 8 | ∞ | 2.1646 | 2.19048 | 32.77 |
| 9 | ∞ | 0.0989 | 1. | |
| 10 | 3.9340 | 1.1733 | 1.75844 | 52.08 |
| 11 | −1.2470 | 0.4329 | 1.85504 | 23.59 |
| 12 | −7.2735 | 1.3977 | 1. | |
| 13 | 3.8701 | 0.7421 | 1.51825 | 63.94 |
| 14 | ∞ | 0.0124 | 1.52233 | 52.71 |
| 15 | ∞ | 0.4948 | 1.50700 | 63.00 |
| 16 | ∞ | | | | f = 1, IH = 0.784, W = 49.537°
d/f = 1.310
d/IH = 1.670
D1/f = 2.149
D2/f = 3.222
D1/D2 = 0.667
|f1|/f = 0.816
f2/f = 2.037

G1f/f = 3.270
G2f/f = 3.389
G1f/G2f = 0.965

Embodiment 6

FIG. 30 shows the optical configuration of an objective system 2F of an oblique-viewing endoscope 1F in Embodiment 6. The basic configuration of the objective system 2F in the present embodiment is similar to that of the objective system 2A in Embodiment 1. The same reference characters are used for the same components as those in Embodiment 1, and the description for the same components will not be repeated. In the objective system 2F in the present embodiment, the rear lens group G2 is constituted by a single positive lens. Because the number of lens components is reduced, the objective system 2F is compact and has a reduced lens length particularly at the rear of the prism P provided as a visual field converting element. However, since the rear lens group G2 is not constituted by a negative lens or a cemented lens, the objective system 2F is incapable of easily correcting a chromatic aberration. It is therefore preferable to use the objective system 2F in a case where the number of pixels of the image pickup device is small and the influence of a chromatic aberration does not appear easily in the image quality.

FIGS. 31A to 31D are aberration diagrams of the objective system 2F in the present embodiment.

Numeric data on Embodiment 6 is shown below.

| Surface No. | r | d | n(e) | ν(e) |
|---|---|---|---|---|
| 1 | ∞ | 0.3714 | 1.88814 | 40.53 |
| 2 | 0.6713 | 0.5323 | 1. | |
| 3 | ∞ | 0.3838 | 1.51564 | 74.74 |
| 4 | ∞ | 0.1898 | 1. | |
| 5 | 7.1542 | 1.3618 | 1.75844 | 52.08 |
| 6 | −1.4385 | 0.1857 | 1. | |
| 7(Stop) | ∞ | 0.0371 | 1. | |
| 8 | ∞ | 2.1665 | 1.88815 | 40.52 |
| 9 | ∞ | 0.1149 | 1. | |
| 10 | 5.9887 | 0.9904 | 1.75844 | 52.08 |
| 11 | −9.5806 | 1.0488 | 1. | |
| 12 | ∞ | 0.7428 | 1.51825 | 63.94 |
| 13 | ∞ | 0.0124 | 1.52233 | 52.71 |
| 14 | ∞ | 0.4952 | 1.50700 | 63.00 |
| 15 | ∞ | | | | f = 1, IH = 0.785, W = 49.539°
d/f = 1.485
d/IH = 1.892
D1/f = 2.169
D2/f = 2.553
D1/D2 = 0.850
|f1|/f = 0.756
f2/f = 1.695
G1f/f = 1.759
G2f/f = 4.996
G1f/G2f = 0.352

Embodiment 7

Figure 32:
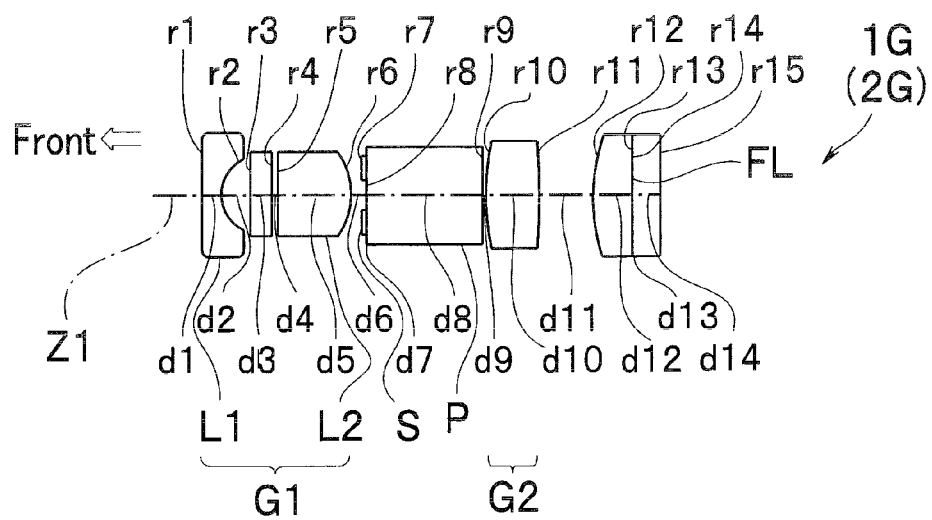
FIG. 32 is a diagram showing the optical configuration of an objective system of an oblique-viewing endoscope in Embodiment 7.

FIG. 32 shows the optical configuration of an objective system 2G of an oblique-viewing endoscope 1G in Embodiment 7. The basic configuration of the objective system 2G in the present embodiment is similar to that of the objective system 2A in Embodiment 1. The same reference characters are used for the same components as those in Embodiment 1, and the description for the same components will not be repeated. In the objective system 2G in the present embodiment, a field lens FL formed of a flat lens having positive refractive power is disposed immediately before the image pickup device, as in the objective system 2E in Embodiment 5. Further, since the rear lens group G2 includes no negative lens or a cemented lens, the objective system 2G is incapable of easily correcting a chromatic aberration, as is the objective system 2F in Embodiment 6. However, the entire objective system 2G is compact. FIGS. 33A to 33D are aberration diagrams of the objective system 2G in the present embodiment.

Numeric data on Embodiment 7 is shown below.

| Surface No. | r | d | n(e) | ν(e) |
|---|---|---|---|---|
| 1 | ∞ | 0.3712 | 1.88814 | 40.53 |
| 2 | 0.6878 | 0.5321 | 1. | |
| 3 | ∞ | 0.3836 | 1.51564 | 74.74 |
| 4 | ∞ | 0.1856 | 1. | |
| 5 | 5.9268 | 1.3612 | 1.75844 | 52.08 |
| 6 | −1.4510 | 0.1856 | 1. | |
| 7(Stop) | ∞ | 0.0371 | 1. | |
| 8 | ∞ | 2.1656 | 1.88815 | 40.52 |
| 9 | ∞ | 0.0875 | 1. | |
| 10 | 5.1500 | 0.9731 | 1.48915 | 70.04 |
| 11 | −8.3062 | 1.0271 | 1. | |
| 12 | 3.4615 | 0.7425 | 1.51825 | 63.94 |
| 13 | ∞ | 0.0124 | 1.52233 | 52.71 |
| 14 | ∞ | 0.4950 | 1.50700 | 63.00 |
| 15 | ∞ | | | |

$f = 1$, $IH = 0.785$, $W = 49.566°$
$d/f = 1.457$
$d/IH = 1.857$
$D1/f = 2.164$
$D2/f = 2.594$
$D1/D2 = 0.834$
$|f1|/f = 0.774$
$f2/f = 1.670$
$G1f/f = 1.721$
$G2f/f = 3.738$
$G1f/G2f = 0.461$

Embodiment 8

FIG. 34 shows the optical configuration of an objective system 2H of an oblique-viewing endoscope 1H in Embodiment 8. The basic configuration of the objective system 2H in the present embodiment is similar to that of the objective system 2A in Embodiment 1. The same reference characters are used for the same components as those in Embodiment 1, and the description for the same components will not be repeated. In the objective system 2H in the present embodiment, a stop SH is disposed between a negative lens constituting the front lens group G1 and a positive lens also constituting the front lens group G1. In the objective system 2H in the present embodiment, the stop SH is disposed in the vicinity of the negative lens provided as a first lens L1. For this reason, the objective system SH is capable of reducing the ray height at the first lens L1 in particular and reducing the lens outside and is, therefore, capable of reducing an image cut-off.

Figure 35:
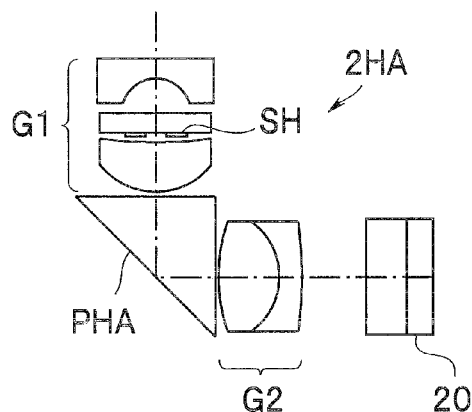
FIG. 35 is a diagram showing a disposition in a case where the objective system of the oblique-viewing endoscope in Embodiment 8 is configured as a side-viewing optical system.
Figure 36:
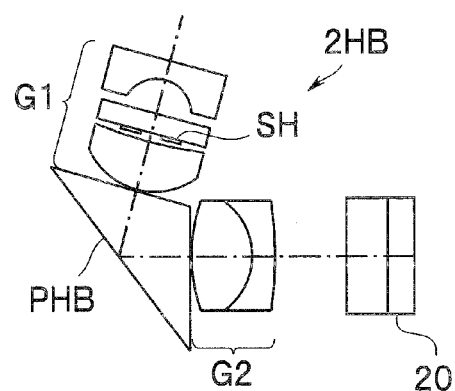
FIG. 36 is a diagram showing a disposition in a case where the objective system of the oblique-viewing endoscope in Embodiment 8 is configured as a rearward-oblique-viewing optical system.
Figure 37A:
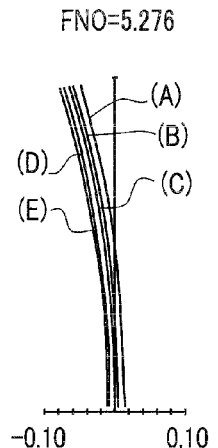
FIGS. 37A to 37D are aberration diagrams of the objective system of the oblique-viewing endoscope in Embodiment 8.
Figure 37B:
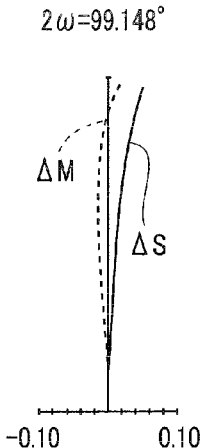
Figure 37C:
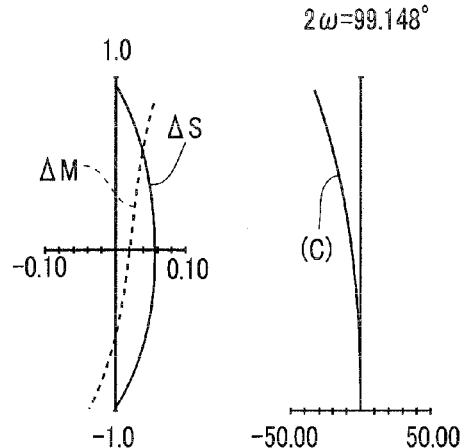
Figure 37D:
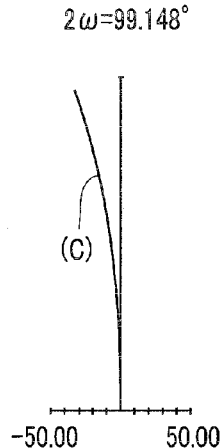

FIG. 35 is a disposition diagram of an objective system 2HA of a side-viewing optical system configured by including a prism PHA provided as a visual field direction converting element for side-viewing observation. FIG. 36 is a disposition diagram of an objective system 2HB of a rearward-oblique-viewing optical system configured by including a prism PHB for rearward-oblique-viewing angle 15°. FIGS. 37A to 37D are aberration diagrams of the objective system 2H in the present embodiment.

Numeric data on Embodiment R is shown below.

| Surface No. | r | d | n(e) | ν(e) |
|---|---|---|---|---|
| 1 | ∞ | 0.3679 | 1.88814 | 40.53 |
| 2 | 0.6410 | 0.6499 | 1. | |
| 3 | ∞ | 0.3801 | 1.51564 | 74.74 |
| 4(Stop) | ∞ | 0.0368 | 1. | |
| 5 | ∞ | 0.1226 | 1. | |
| 6 | −5.6549 | 0.8640 | 1.75844 | 52.08 |
| 7 | −1.2481 | 0.0981 | 1. | |
| 8 | ∞ | 2.6117 | 1.88815 | 40.52 |
| 9 | ∞ | 0.0491 | 1. | |
| 10 | 3.4943 | 1.1649 | 1.75844 | 52.08 |
| 11 | −1.2326 | 0.4292 | 1.85504 | 23.59 |
| 12 | −6.8473 | 1.3243 | 1. | |
| 13 | ∞ | 0.7357 | 1.51825 | 63.94 |
| 14 | ∞ | 0.0123 | 1.52233 | 52.71 |
| 15 | ∞ | 0.4905 | 1.50700 | 63.00 |
| 16 | ∞ | | | |

$f = 1$, $IH = 0.777$, $W = 49.574°$
$d/f = 1.530$
$d/IH = 1.969$
$D1/f = 1.844$
$D2/f = 3.085$
$D1/D2 = 0.598$
$|f1|/f = 0.722$
$f2/f = 1.947$
$G1f/f = 3.377$
$G2f/f = 3.960$
$G1f/G2f = 0.853$

Embodiment 9

FIG. 38 shows the optical configuration of an objective system 2I of an oblique-viewing endoscope 1I in Embodiment 9. The objective system 2I in the present embodiment has a lens configuration similar to that of the objective system 2H in Embodiment R Nit differs from the objective system 2H in that a high-refraction material having a refractive index of 2 or more is used as the material of a prism PI. In the objective system 2I in the present embodiment, the air-converted length of the prism PI is short. FIGS. 39A to 39D are aberration diagrams of the objective system 2I in the present embodiment.

Numeric data on Embodiment 9 is shown below.

| Surface No. | r | d | n(e) | ν(e) |
|---|---|---|---|---|
| 1 | ∞ | 0.3684 | 1.88814 | 40.53 |
| 2 | 0.6404 | 0.6508 | 1. | |
| 3 | ∞ | 0.3806 | 1.51564 | 74.74 |
| 4(Stop) | ∞ | 0.0368 | 1. | |
| 5 | ∞ | 0.1228 | 1. | |
| 6 | −5.9280 | 0.8901 | 1.79012 | 43.95 |
| 7 | −1.2946 | 0.0982 | 1. | |
| 8 | ∞ | 2.6154 | 2.01169 | 28.07 |
| 9 | ∞ | 0.0491 | 1. | |
| 10 | 3.5546 | 1.1665 | 1.75844 | 52.08 |
| 11 | −1.2183 | 0.4298 | 1.85504 | 23.59 |
| 12 | −7.0474 | 1.3261 | 1. | |
| 13 | ∞ | 0.7367 | 1.51825 | 63.94 |
| 14 | ∞ | 0.0123 | 1.52233 | 52.71 |
| 15 | ∞ | 0.4912 | 1.50700 | 63.00 |
| 16 | ∞ | | | |

$f = 1$, $IH = 0.778$, $W = 49.591°$
$d/f = 1.447$
$d/IH = 1.859$

-continued

D1/f = 1.852
D2/f = 3.089
D1/D2 = 0.599
|f1|/f = 0.721
f2/f = 1.932
G1f/f = 3.192
G2f/f = 4.076
G1f/G2f = 0.783

Embodiment 10

Figure 40:
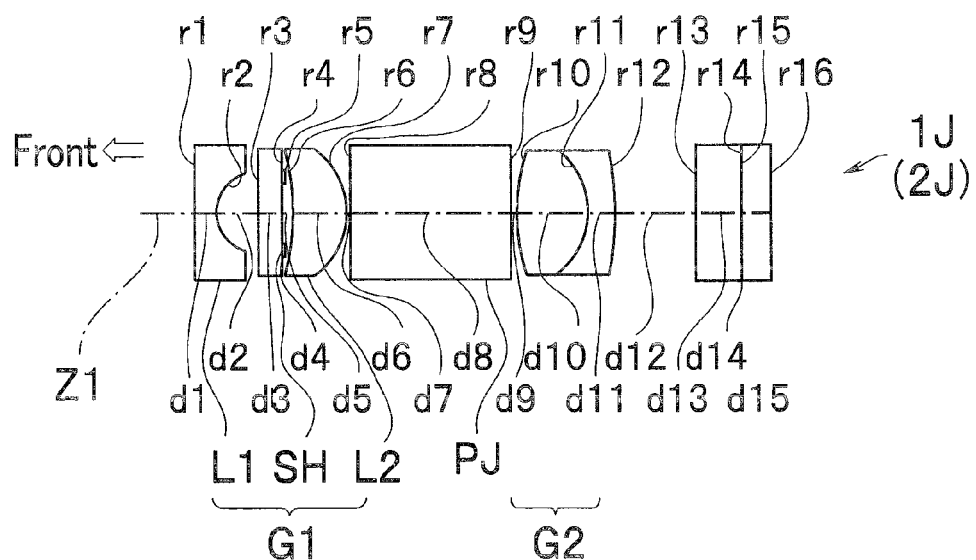
FIG. 40 is a diagram showing the optical configuration of an objective system of an oblique-viewing endoscope in Embodiment 10.
Figure 41A:
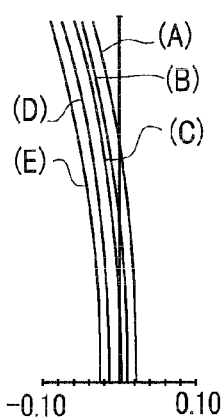
FIGS. 41A to 41D are aberration diagrams of the objective system of the oblique-viewing endoscope in Embodiment 10.
Figure 41B:
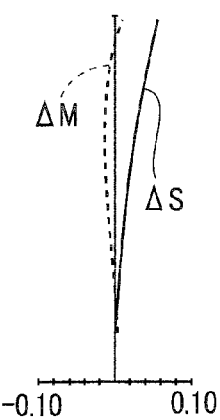
Figure 41C:
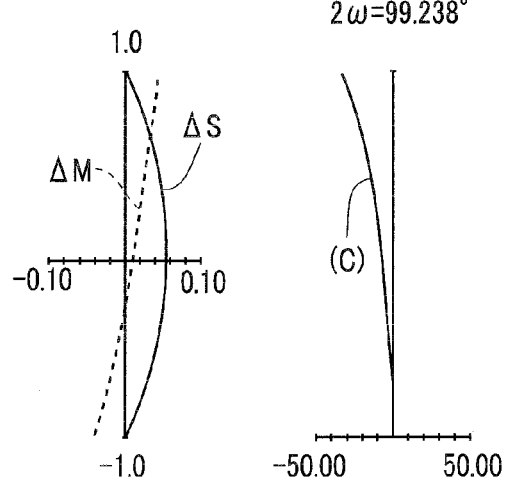
Figure 41D:
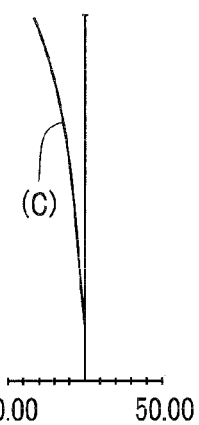

FIG. 40 shows the optical configuration of an objective system 2J of an oblique-viewing endoscope 1J in Embodiment 10. The objective system 2J in the present embodiment has a lens configuration similar to those of the objective system 2H in Embodiment 8 and the objective system 2I in Embodiment 9 but differs from the objective systems 2H and 2I in that a crystalline material of a high refractive index of 2.1 or more is used as the material of a prism PJ. In the objective system 2J in the present embodiment, the air-converted length of the prism PI is short because of use of the high-refractive-index material. An ordinary optical glass having a refractive index of 1.9 or more has an Abbe constant of 30 or less, that is, dispersion therein is markedly large. However, a material having a refractive index of 1.9 or more but having an Abbe constant of 30 or more exists in transparent crystalline materials. Use of such a material is effective in color correction or the like. FIGS. 41A to 41D are aberration diagrams of the objective system 2J in the present embodiment.

Numeric data on Embodiment 10 is shown below.

| Surface No. | r | d | n(e) | v(e) |
|---|---|---|---|---|
| 1 | ∞ | 0.3690 | 1.88814 | 40.53 |
| 2 | 0.6367 | 0.6520 | 1. | |
| 3 | ∞ | 0.3813 | 1.51564 | 74.74 |
| 4(Stop) | ∞ | 0.0369 | 1. | |
| 5 | ∞ | 0.1230 | 1. | |
| 6 | −6.2483 | 0.8764 | 1.79012 | 43.95 |
| 7 | −1.2891 | 0.0984 | 1. | |
| 8 | ∞ | 2.6201 | 2.19048 | 32.77 |
| 9 | ∞ | 0.0492 | 1. | |
| 10 | 3.6183 | 1.1686 | 1.75844 | 52.08 |
| 11 | −1.1863 | 0.4305 | 1.85504 | 23.59 |
| 12 | −7.0333 | 1.3285 | 1. | |
| 13 | ∞ | 0.7381 | 1.51825 | 63.94 |
| 14 | ∞ | 0.0123 | 1.52233 | 52.71 |
| 15 | ∞ | 0.4920 | 1.50700 | 63.00 |
| 16 | ∞ | | | | f = 1, IH = 0.78, W = 49.619°
d/f = 1.344
d/IH = 1.723
D1/f = 1.847
D2/f = 3.095
D1/D2 = 0.597
|f1|/f = 0.717
f2/f = 1.907
G1f/f = 3.067
G2f/f = 4.163
G1f/G2f = 0.737

Embodiment 11

FIG. 42 shows the optical configuration of an objective system 2K of an oblique-viewing endoscope 1K in Embodiment 11. The objective system 2K in the present embodiment has a lens configuration similar to that of the objective system 2H in Embodiment 8 but differs from the objective system 2H in that a cemented lens constituting the rear lens group G2 is constituted by a negative lens and a positive lens disposed in this order from the object side. FIGS. 43A to 43D are aberration diagrams of the objective system 2K in the present embodiment.

Numeric data on Embodiment 11 is shown below.

| Surface No. | r | d | n(e) | v(e) |
|---|---|---|---|---|
| 1 | ∞ | 0.3707 | 1.88814 | 40.53 |
| 2 | 0.6688 | 0.6550 | 1. | |
| 3 | ∞ | 0.3831 | 1.51564 | 74.74 |
| 4(Stop) | ∞ | 0.0371 | 1. | |
| 5 | ∞ | 0.1145 | 1. | |
| 6 | −4.0227 | 0.8650 | 1.79012 | 43.95 |
| 7 | −1.2341 | 0.0989 | 1. | |
| 8 | ∞ | 2.6320 | 1.88815 | 40.52 |
| 9 | ∞ | 0.0495 | 1. | |
| 10 | 3.2080 | 0.3089 | 1.85504 | 23.59 |
| 11 | 1.1366 | 1.1739 | 1.75844 | 52.08 |
| 12 | −9.0093 | 1.3346 | 1. | |
| 13 | ∞ | 0.7414 | 1.51825 | 63.94 |
| 14 | ∞ | 0.0124 | 1.52233 | 52.71 |
| 15 | ∞ | 0.4943 | 1.50700 | 63.00 |
| 16 | ∞ | | | | f = 1, IH = 0.783, W49.558°
d/f = 1.542
d/IH = 1.969
D1/f = 1.838
D2/f = 3.043
D1/D2 = 0.604
|f1|/f = 0.753
f2/f = 1.982
G1f/f = 3.364
G2f/f = 3.916
G1f/G2f = 0.859

Embodiment 12

Figure 44:
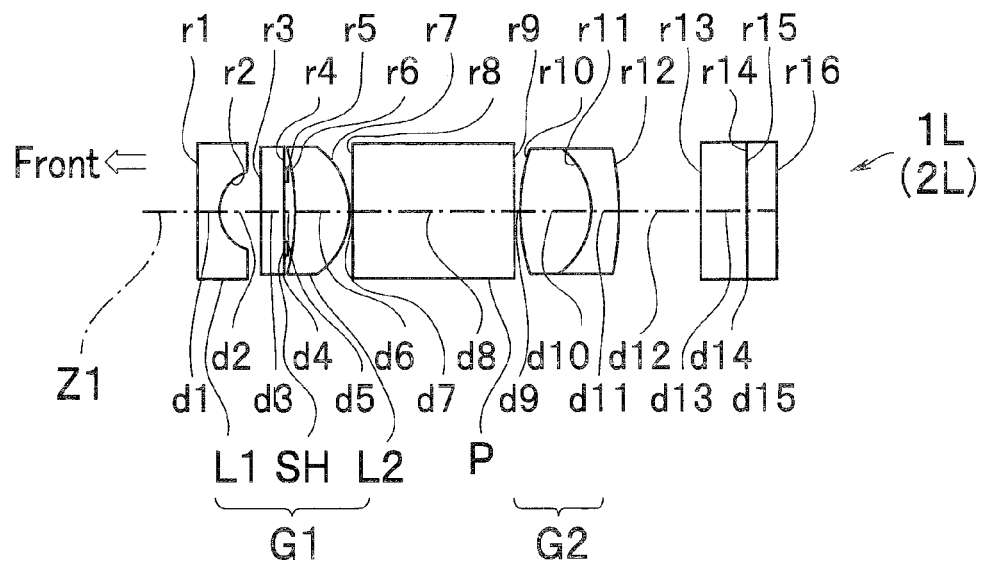
FIG. 44 is a diagram showing the optical configuration of an objective system of an oblique-viewing endoscope in Embodiment 12.
Figure 45A:
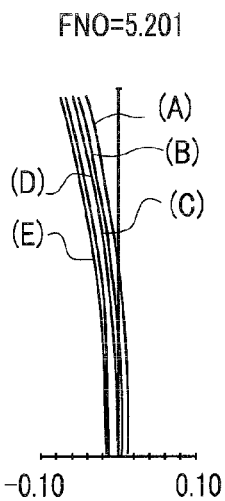
FIGS. 45A to 45D are aberration diagrams of the objective system of the oblique-viewing endoscope in Embodiment 12.
Figure 45B:
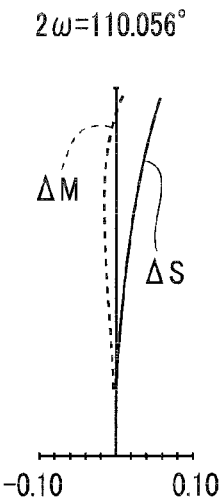
Figure 45C:
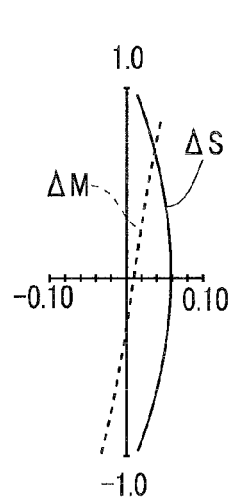
Figure 45D:
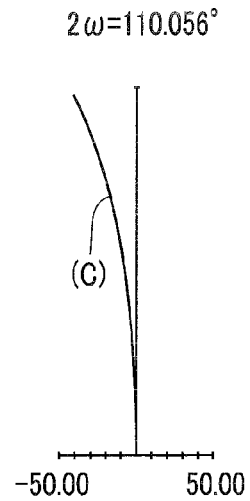

FIG. 44 shows the optical configuration of an objective system 2L of an oblique-viewing endoscope 1L in Embodiment 12. The objective system 2L in the present embodiment is obtained by increasing the field of view 2ω to a wide angle of 110° in a lens configuration similar to that of the objective system 2H in Embodiment 8, and is capable of wide-scope observation. FIGS. 45A to 45D are aberration diagrams of the objective system 2L in the present embodiment.

Numeric data on Embodiment 12 is shown below.

| Surface No. | r | d | n(e) | v(e) |
|---|---|---|---|---|
| 1 | ∞ | 0.3952 | 1.88814 | 40.53 |
| 2 | 0.6755 | 0.7825 | 1. | |
| 3 | ∞ | 0.4084 | 1.51564 | 74.74 |
| 4(Stop) | ∞ | 0.0395 | 1. | |
| 5 | ∞ | 0.0865 | 1. | |
| 6 | −5.6238 | 0.9162 | 1.75844 | 52.08 |
| 7 | −1.3473 | 0.1054 | 1. | |
| 8 | ∞ | 2.8058 | 1.88815 | 40.52 |
| 9 | ∞ | 0.0527 | 1. | |
| 10 | 3.6308 | 1.1771 | 1.75844 | 52.08 |
| 11 | −1.3689 | 0.4016 | 1.85504 | 23.59 |
| 12 | −6.7441 | 1.4203 | 1. | |
| 13 | ∞ | 0.7904 | 1.51825 | 63.94 |
| 14 | ∞ | 0.0132 | 1.52233 | 52.71 |
| 15 | ∞ | 0.5269 | 1.50700 | 63.00 |
| 16 | ∞ | | | | f = 1, IH = 0.835, W55.028°
d/f = 1.644

-continued

| Surface No. | r | d | n(e) | v(e) |
|---|---|---|---|---|
| d/IH = 1.969 | | | | |
| D1/f = 2.014 | | | | |
| D2/f = 3.238 | | | | |
| D1/D2 = 0.622 | | | | |
| |f1|/f = 0.761 | | | | |
| f2/f = 2.13844 | | | | |
| G1f/f = 3.807 | | | | |
| G2f/f = 3.950 | | | | |
| G1f/G2f = 0.964 | | | | |

Embodiment 13

Figure 46:
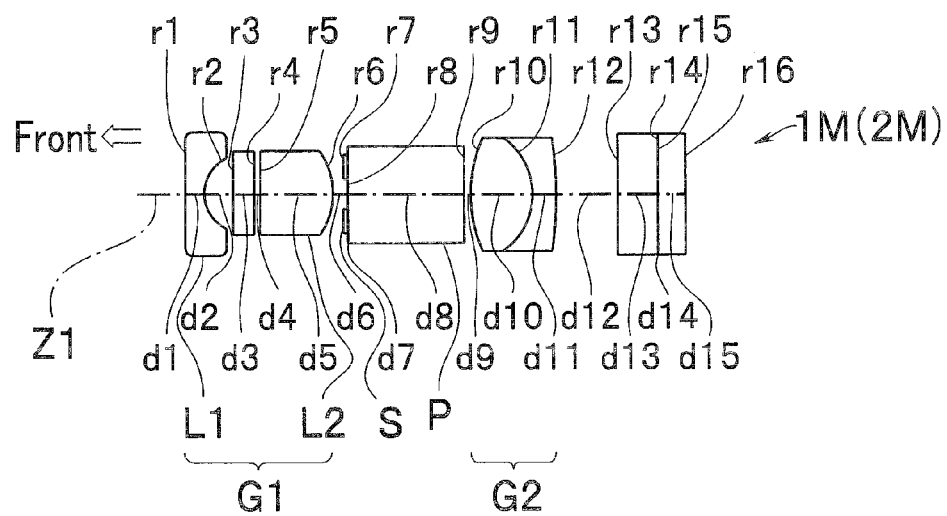
FIG. 46 is a diagram showing the optical configuration of an objective system of an oblique-viewing endoscope in Embodiment 13.
Figure 47A:
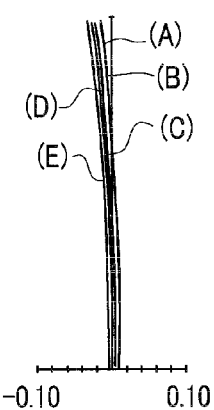
FIGS. 47A to 47D are aberration diagrams of the objective system of the oblique-viewing endoscope in Embodiment 13.
Figure 47B:
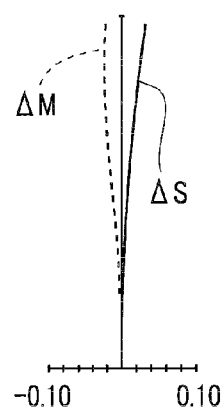
Figure 47C:
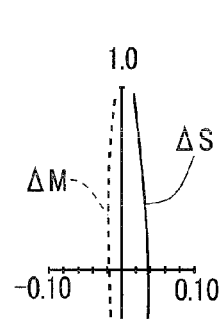
Figure 47D:
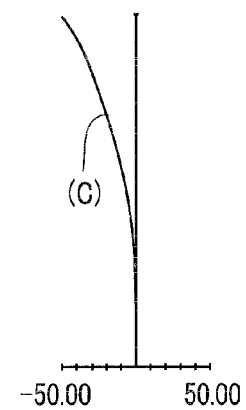

FIG. 46 shows the optical configuration of an objective system 2M of an oblique-viewing endoscope 1M in Embodiment 13. The objective system 2M in the present embodiment is obtained by increasing the field of view to a wide field of 120° in a lens configuration similar to that of the objective system 2A in Embodiment 1, and is capable of observing through a wide scope at a time. FIGS. 47A to 47D are aberration diagrams of the objective system 2M in the present embodiment.

Numeric data on Embodiment 13 is shown below.

| Surface No. | r | d | n(e) | v(e) |
|---|---|---|---|---|
| 1 | ∞ | 0.4136 | 1.88814 | 40.53 |
| 2 | 0.7920 | 0.5928 | 1. | |
| 3 | ∞ | 0.4274 | 1.51564 | 74.74 |
| 4 | ∞ | 0.2757 | 1. | |
| 5 | ∞ | 1.5164 | 1.75844 | 52.08 |
| 6 | −1.7444 | 0.2757 | 1. | |
| 7(Stop) | ∞ | 0.0414 | 1. | |
| 8 | ∞ | 2.4125 | 1.88815 | 40.52 |
| 9 | ∞ | 0.1103 | 1. | |
| 10 | 2.9333 | 1.1029 | 1.75844 | 52.08 |
| 11 | −1.3716 | 0.5514 | 1.85504 | 23.59 |
| 12 | −11.2103 | 1.0094 | 1. | |
| 13 | ∞ | 0.8271 | 1.51825 | 63.94 |
| 14 | ∞ | 0.0138 | 1.52233 | 52.71 |
| 15 | ∞ | 0.5514 | 1.50700 | 63.00 |
| 16 | ∞ | | | | f = 1, IH = 0.874, W = 59.128°
d/f = 1.705
d/IH = 1.951
D1/f = 2.549
D2/f = 2.964
D1/D2 = 0.860
|f1|/f = 0.892
f2/f = 2.300
G1f/f = 3.392
G2f/f = 3.862
G1f/G2f = 0.878

FIG. 48 shows the values of condition expressions with respect to the embodiments.

As described above, the objective system 2 of the oblique-viewing endoscope 1 in each embodiment has a front lens group G1 having a positive refractive power, a prism P disposed on the CCD 20 side of the front lens group G1 and a rear lens group G2 disposed on the CCD 20 side of the prism P and having a positive refractive power. The objective system 2 can contribute to a reduction in diameter of the distal end portion 5 by the optimum lens configuration designed to improve the observation performance in correspondence with the reduction size of the CCD 20 and the increase in the number of pixels. Further, the objective system 2 satisfies each condition expression as shown in FIG. 48. Therefore, various aberrations are suitably corrected in the objective system 2.

Embodiments of assembly adjustment in the objective system 2 of the oblique-viewing endoscope 1 according to the present invention will next be described.

Embodiment 14

As shown in FIGS. 49 to 50, an objective system N for oblique viewing has a front lens group G1 provided in front of a prism P provided as a visual field direction converting element, and a rear lens group G2 provided at the rear of the prism P. The front lens group θ1 is disposed in one lens unit frame (first lens unit frame) F1 to form an integral front lens group unit U1. Also, as shown in FIG. 50, the front lens group unit U1 is disposed in a lens unit frame (second lens unit frame) F2 in which a rear lens group unit U2 integrally configured of the prism P and the rear lens group G2 is disposed, thus configuring the objective system 2N.

As shown in FIG. 50, the objective system 2N is configured so that the front lens group unit U1 can be rotated relative to the rear lens group unit U2 to enable striking a balance between an amount of lens eccentricity produced in the front lens group unit U1 and an amount of lens eccentricity produced in the rear lens group G2 at the rear of the prism P. In this way, eccentricity adjustment can be performed in the entire objective system. In the objective system 2N, a deviation angle adjustment, an adjustment of field of view and a partial defocus adjustment in particular can be made through the eccentricity adjustment. After the eccentricity adjustment, the gap between the front lens group unit U1 and the lens unit frame F2 of the rear lens group unit U2 supporting the front lens group unit U1 is filled with an adhesive to fix the units to each other and to simultaneously seal the gap in order to prevent penetration of moisture from the outside.

As in the case of an objective system 2P shown in FIG. 51, adjusting screws SW mounted in the lens unit frame F2 of the rear lens group unit U2 may be used instead of the adhesive to fix the front lens group unit U1. Adjustment described below with adjusting screws SW as in the objective system 2P can be easily performed. After eccentricity adjustment, the gap between the front lens group unit U1 and the lens unit frame F2 of the rear lens group unit U2 supporting the front lens group unit U1 is filled with an adhesive to seal the gap. In some case of adjustment by lens unit rotation, adjustment to attain an adjusted value within a predetermined range cannot be performed even by largely rotating the front lens group unit U1 if the amount of lens eccentricity in the front lens group unit U1 is small. In such a case, adjustment is performed by making the entire front lens group unit U1 eccentric.

Embodiment 15

In an objective system 2Q in Embodiment 15, as shown in FIG. 52, a gap G is provided between an outer lens unit frame F2 holding a front lens unit U1 and a lens unit frame F1 of a front lens group unit U1, and adjustment can be performed by changing the position of the entire front lens group unit U1 relative to the rear lens group unit U2. FIG. 52 shows an example of shift adjustment by moving the front lens group unit U1 relative to the rear lens group unit U2 in a direction perpendicular to the optical axis Z1. In this case, an adjustment jig (not shown) which perpendicularly holds the front lens group unit U1 may be used to facilitate the adjustment operation. After eccentricity adjustment, the gap G between the lens unit frame F1 and the lens unit frame F2 is filled with an adhesive to fix the lens units and to seal the gap. The size of the gap G for adjustment may be determined from the necessary amount of eccentricity adjustment computed on the basis of an amount of lens variation predicted in the objective system 2Q for oblique viewing.

In the objective system 2Q, the gap G for adjustment sealed with an adhesive also exists between the lens unit U1 and the lens unit U2. However, separation cannot occur easily between the metallic lens unit frames F1 and F2 and the adhesive. Therefore, a fog on in the objective system is not easily caused by penetration of moisture from the outside. Also, there is no gap between the front lens group G1 and the lens unit frame F1, and the possibility of penetration of moisture through the region between the front lens group G1 and the lens unit frame F1 is low. Therefore a fog in the objective system 2G is not easily caused.

Embodiment 16

Figure 53:
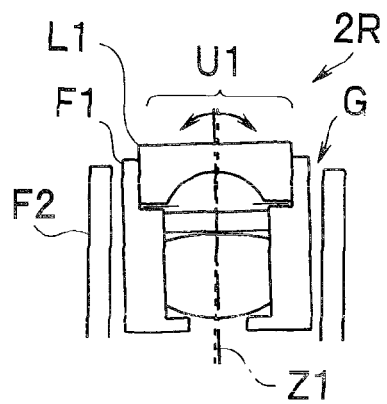
FIG. 53 is a diagram for explaining tilt adjustment of a front lens group unit with respect to a rear lens group unit, showing a section of a structure taken along an optical axis.

FIG. 53 shows an example of tilt adjustment performed as eccentricity adjustment by tilting a front lens unit U1 of an objective system 2R for oblique viewing with respect to the optical axis Z1. With tilt adjustment, there is, conversely, a risk of causing a partial defocus and a reduction in image quality if the amount of eccentricity adjustment is large. However, degradation in image quality can be prevented if the amount of eccentricity of the lenses including the rear lens group unit U2 is set small in advance.

Figure 54:
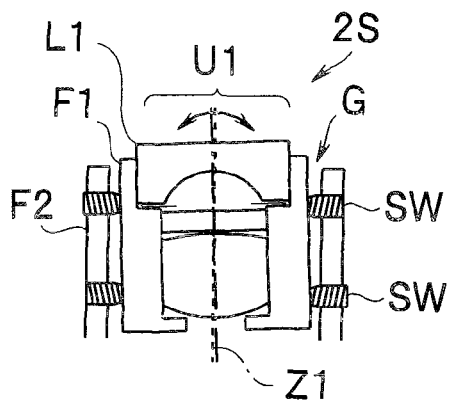
FIG. 54 is a diagram for explaining a concrete example of tilt adjustment of a front lens group unit with respect to a rear lens group unit, showing a section of a structure taken along an optical axis.

Tilt adjustment is advantageous in enabling eccentricity adjustment through adjustment by a small amount of tilt. Conversely, tilt adjustment necessitates a fine adjustment, and an operation for tilting in the desired direction is difficult to perform in some case. However, adjusting screws SW may be provided in several upper and lower positions in the lens unit frame F2, as shown in an objective system 2S in FIG. 54. A minute amount of tilt of the lens unit U1 can be adjusted by suitably fastening the adjusting screws SW. After eccentricity adjustment, a gap G is sealed by filling with a sealing material.

Embodiment 17

Figure 55:
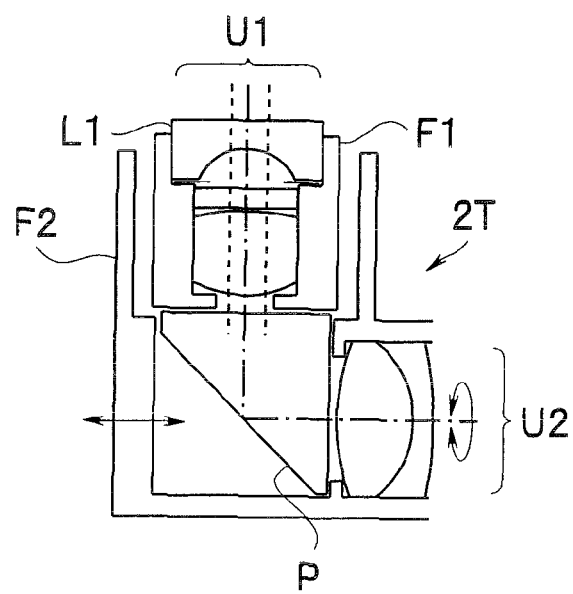
FIG. 55 is a diagram for explaining adjustment performed by shifting or rotating a rear lens unit with respect to a front lens group unit, showing a section of a structure taken along an optical axis.

FIG. 55 shows an objective system 2T in which an adjustment in a top-bottom direction of the view is made through shift adjustment of a rear lens group U2 unit including a prism P, and in which an adjustment in a left-right direction of the view is made by rotating the rear lens group unit U2. In an actual adjustment operation, an adjustment is made by moving the rear lens group unit U2 while fixing a front lens group unit U1. Needless to say, an adjustment may be made while the front lens group unit U1 is fixed on a predetermined jig.

Also, tilt adjustment may be performed after performing rotational adjustment or shift adjustment of the front lens group unit U1. In the objective system 2T, a plurality of adjustment methods are used, so that the respective amounts of adjustment by the methods can be reduced.

As described above, the objective system 2 of the oblique-viewing endoscope 1 in each embodiment has a first lens unit frame F1 in which a front lens group G1 is disposed and a second lens unit frame F2 in which a rear lens group G2, a prism P and the first lens unit frame F1 are disposed, and the first lens unit U1 disposed in the first lens unit frame F1 is made eccentric relative to the second lens unit U2 disposed in the second lens unit frame F2 to be optically adjusted. Therefore, variations in performance of the objective system of the oblique-viewing endoscope 1 are small. Also, the objective system is free from having an observed image made difficult to see as a result of fogging caused by penetration of moisture from the outside and dew condensation of water vapor on a lens inner surface. That is, the objective system 2 is capable of implementing an adjustment method which reduces the occurrence of a fog and limits deteriorations in optical performance at the time of assembly adjustment.

In assembly adjustment in the objective system 2, as described above, adjustment can be performed by performing one of an operation for rotating the first lens unit U1 or the second lens unit U2 relative to the other unit, an operation for shifting one of the two lens units relative to the other and an operation for tilting one of the two lens units relative to the other, or a combination of some of these operations.

Embodiments of the layout in the distal end portion 5 of the oblique-viewing endoscope 1 according to the present invention will be described.

Embodiment 18

Figure 56:
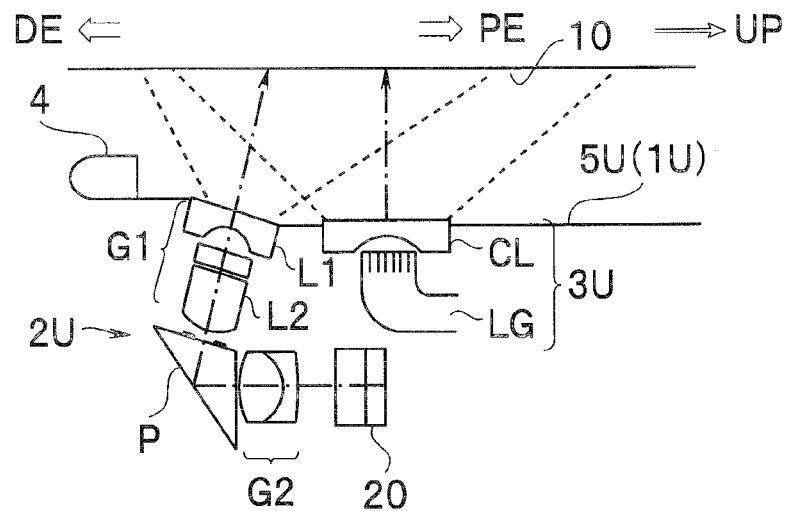
FIG. 56 is a diagram showing a disposition of an objective system and an illumination system in an oblique-viewing endoscope of the present invention.

FIG. 56 shows a distal end portion 5U of an endoscope 1U in Embodiment 18 having an objective system 2U and an illumination system 3U disposed in this order from the distal end DE side, in other words, having an illumination system 3U disposed on the proximal end PE side relative to an objective system 2U.

The objective system 2U of the endoscope 1U is constituted by a front lens group G1 including a negative flat lens having positive refractive power (L1) and a lens having positive refractive power on both sides (L2), a prism P provided as a visual field direction converting element, and a rear lens group G2 formed of a cemented lens. A CCD 20, which is an image pickup device, is provided at the rear of the rear lens group G2. The prism P in the objective system 2U is formed so that the rearward-viewing angle ($\theta 1$) is 15°.

In the illumination system 3U, a distal end portion of a light guide LG is bent into a rounded shape, and an illumination lens CL, which is a lens having negative refractive power, is disposed at the distal end of the light guide LG. Rays emitted from a center of the light guide LG are applied to an object 10 to be observed or photographed by being transmitted through a center of the illumination lens CL. The direction of illumination from the illumination system 3 is generally perpendicular to the longitudinal direction of the endoscope 1U. The layout in the distal end portion 5U is such that $\theta 1=15°$, $\theta 2=0$, L=4 mm, and D=15 mm (see FIG. 14).

As described above, the oblique-viewing endoscope 1 in each embodiment has an illumination optical system 3 disposed on the proximal end PE side relative to the objective system 2. Thus, the oblique-viewing endoscope 1 has, in particular, an optimum endoscope distal end portion capable of reducing the influence of an image cut-off or the like caused by a forceps rising base 6 or the like, and obtaining a good luminous intensity distribution for maintaining the desired lightness at a visual field peripheral portion even when the scope of the field of view for observation is increased, is stable in optical performance, and has good treatment performance.

Embodiment 19

Figure 57:
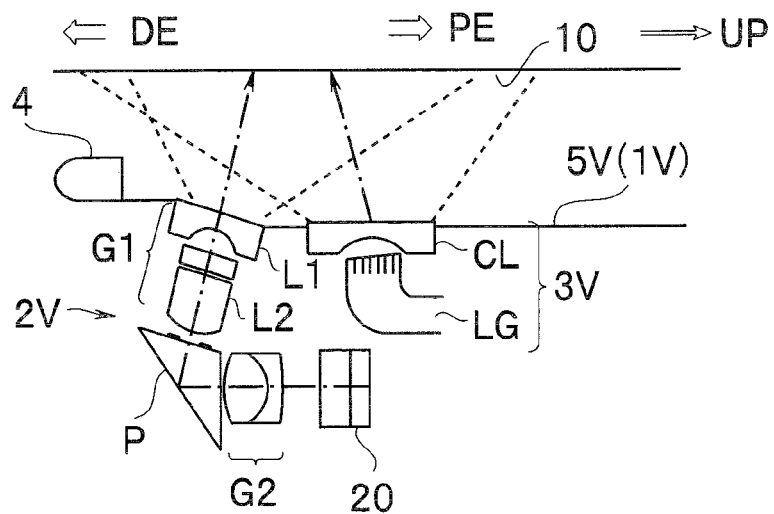
FIG. 57 is a diagram showing a disposition of an objective system and an illumination system in an oblique-viewing endoscope of the present invention.

FIG. 57 shows an endoscope 1V in Embodiment 19 having a distal end portion 5V in which an objective system 2V and an illumination system 3V are disposed in this order from the distal end DE side. The objective system 2V in the present embodiment is similar to the objective system 2U in Embodiment 18. The illumination system 3V is configured so that the lightness in the view at the time of closeup observation is made more uniform than that in the case of the illumination system 3U. That is, in the illumination system 3V, as shown in FIG. 57, a distal end portion of the light guide LG is cut slantingly with respect to the longitudinal direction of the endoscope 1V. Rays emitted from a center of the light guide LG are thereby caused to travel in a direction inclined toward the distal end DE side of the endoscope 1V after being transmitted through the illumination lens CL to be applied to the object 10 at an illumination angle θ2 of 7.5° from a direction perpendicular to the longitudinal direction of the endoscope 1V. The endoscope 1V is capable of securing sufficient lightness in the field of view at the time of closeup observation in comparison with the endoscope 1U. The layout in the distal end portion 5V is such that θ1=15°, θ2=7.5°, L=4 mm, and D=15 mm (see FIG. 14).

For example, in an endoscope 1 in which the best distance of the objective system 2 is 7 mm, θ2=24° when closeup observation at a distance of 5 mm (L=5 mm, θ1=15° is performed. Accordingly, a setting of the illumination angle θ2 in a range of 0°≤θ2≤25 may be made. However, in the case of using an illumination system 3 designed by placing too much stress on closeup observation, there is a possibility of the luminous intensity distribution being unbalanced at the time of non-closeup observation. It is necessary to exercise care to avoid such a result.

Embodiment 20

Figure 58:
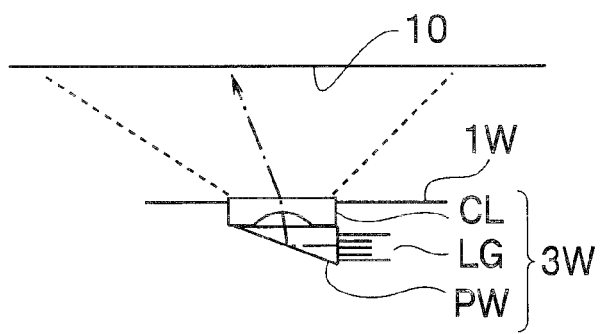
FIG. 58 is a diagram showing a configuration example of an illumination system in an oblique-viewing endoscope of the present invention.

FIG. 58 shows an illumination system 3W of an endoscope 1W in Embodiment 20. In some case of use of a light guide LG as an illumination light source of the oblique-viewing endoscope, a distal end portion of the light guide LG is bent into a rounded shape, as shown in FIG. 56 (Embodiment 18) or FIG. 57 (Embodiment 19). However, if the bending angle is large or the radius of curvature of the bent portion is small, light guide fibers forming the light guide LG can be easily broken and a loss of a quantity of light may result. The illumination system 3W has a prism PW as an illumination direction converting element for changing the direction of illumination without bending a distal end portion of the light guide LG. Saving of space in the diametric direction of the endoscope 1W is thus enabled even in a case where the disposition space is limited for a reason relating to the configuration of the illumination system 3.

Figure 59:
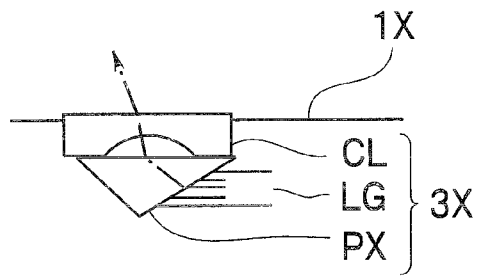
FIG. 59 is a diagram showing a configuration example of an illumination system in an oblique-viewing endoscope of the present invention.

In an illumination system 3X of an endoscope 1X in an example of modification of Embodiment 20 shown in FIG. 59, an end surface of a light guide LG is slantingly cut to be combined with a prism PX provided as an illumination direction converting element. The illumination system 3X has the same effect as that of the illumination system 3W.

Embodiment 21

Figure 60:
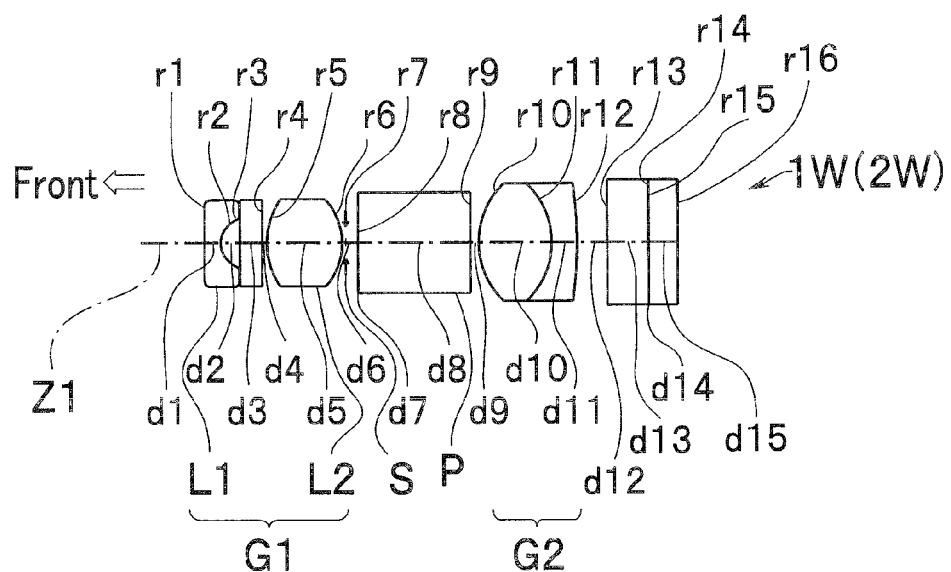
FIG. 60 is a diagram showing the optical configuration of an objective system of an oblique-viewing endoscope in Embodiment 21.
Figures 61A, 61B, 61C, 61D:
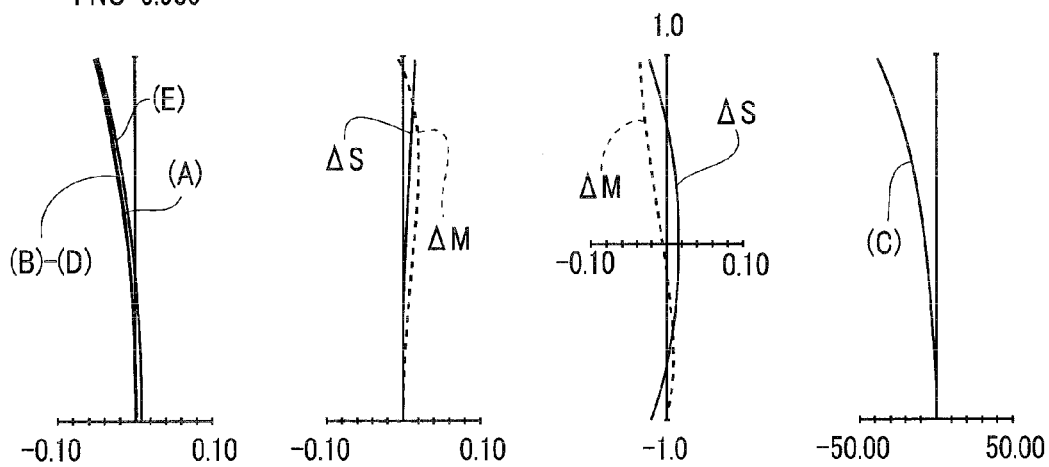
FIGS. 61A to 61D are aberration diagrams of the objective system of the oblique-viewing endoscope in Embodiment 21.

FIG. 60 shows the optical configuration of an objective system 2W of an oblique-viewing endoscope 1W in Embodiment 21. The objective system 2W in the present embodiment has a positive front lens group (front lens group G1) and a positive rear lens group (rear lens group G2), with a prism P interposed therebetween. A stop S is disposed between the front lens group G1 and the prism. That is, in the objective system 2W in the present embodiment, the front lens group G1 constituted by a first lens of a negative refractive power and a second lens of a positive refractive power and having a positive refractive power is disposed in front of the prism P provided as a visual field direction converting element, and the rear lens group G2 constituted by a cemented lens is disposed at the rear of the prism P. The rear lens group G2 is constituted by a cemented lens formed by cementing together a positive lens and a negative lens.

With the reduction in pixel pitch of the image pickup device, a need arises to limit a chromatic aberration to a small amount. To enable this limiting, in the objective system 2W, a low-dispersion glass is used for the positive lenses in the front lens group G1 and the rear lens group G2 and the difference between the refractive indexes of the glass members used for the cemented lens is set to a large value of 0.4 or more. As a result, aberrations are balancedly corrected in the objective system 2W.

The number of lenses in the objective system 2W is small, four, because the cemented lens is included. However, the performance of the objective system 2W is good. The price of the objective system can be limited by reducing the number of lenses. Also, because the stop S is disposed in front of the prism P in the objective system 2W, the ray height at the front lens group G1 is limited and the lens outside diameter is reduced. In particular, the first lens L1 is smaller in size. Also, because the negative and positive lenses are disposed in front of the stop S, the refractive power of the first lens group G1 is well balanced and, therefore, the facility with which corrections of aberrations such as a spherical aberration and a coma are made is improved.

In the objective system 2 of the present invention, not exclusively in the present embodiment, arranging the front lens group G1 and the second lens group G2 so that the surface of the positive lens (single lens or cemented lens) having a smaller radius of curvature in the front lens group G1 faces rearward and the surface of the positive lens (single lens or cemented lens) having a smaller radius of curvature in the second lens group G2 faces forward facilitates balancing of the refractive power of the entire objective system as well as aberration correction.

In an endoscope having an image pickup device such as a CCD 20, electric members such as a circuit board on which electronic parts such as resistors and capacitors are mounted and electric cables are connected to a rear end portion of the CCD 20, and a long space is therefore required for a portion other then the lens system (objective system). In the objective system 2W in the present embodiment, the back focal length is reduced while a sufficiently long prism length is secured. Therefore, the length of the rigid portion in the endoscope distal end portion is short and the operability and the treatment performance are good.

FIGS. 61A to 61D are aberration diagrams of the objective system 2W in the present embodiment.

Numeric data on the present embodiment is shown below.

| Surface No. | r | d | n(e) | ν(e) |
|---|---|---|---|---|
| 1 | ∞ | 0.3455 | 1.88815 | 40.52 |
| 2 | 0.6680 | 0.3847 | 1. | |
| 3 | ∞ | 0.3455 | 1.52266 | 74.72 |
| 4 | ∞ | 0.0461 | 1. | |
| 5 | 1.7679 | 1.6355 | 1.48915 | 70.04 |
| 6 | −1.1621 | 0.0346 | 1. | |
| 7(Stop) | ∞ | 0.1497 | 1. | |
| 8 | ∞ | 2.5684 | 1.88815 | 40.52 |
| 9 | ∞ | 0.1497 | 1. | |
| 10 | 1.3372 | 1.2439 | 1.48915 | 70.04 |
| 11 | −1.3372 | 0.3455 | 1.93429 | 18.74 |
| 12 | −3.9137 | 0.4018 | 1. | |
| 13 | ∞ | 0.4607 | 1.88815 | 40.52 |
| 14 | ∞ | 0.0115 | 1.52233 | 52.71 |
| 15 | ∞ | 0.8062 | 1.61350 | 50.20 |
| 16 | ∞ | | | | f = 1, IH = 0.730, W = 49.730°
d/f = 1.694

-continued

| Surface No. | r | d | n(e) | v(e) |
|---|---|---|---|---|
| d/IH = 2.321 | | | | |
| D1/f = 2.123 | | | | |
| D2/f = 2.317 | | | | |
| D1/D2 = 0.917 | | | | |
| \|f1\|/f = 0.752 | | | | |
| f2/f = 1.755 | | | | |
| G1f/f = 2.834 | | | | |
| G2f/f = 3.394 | | | | |
| G1f/G2f = 0.835 | | | | |

Embodiment 22

Figure 62:
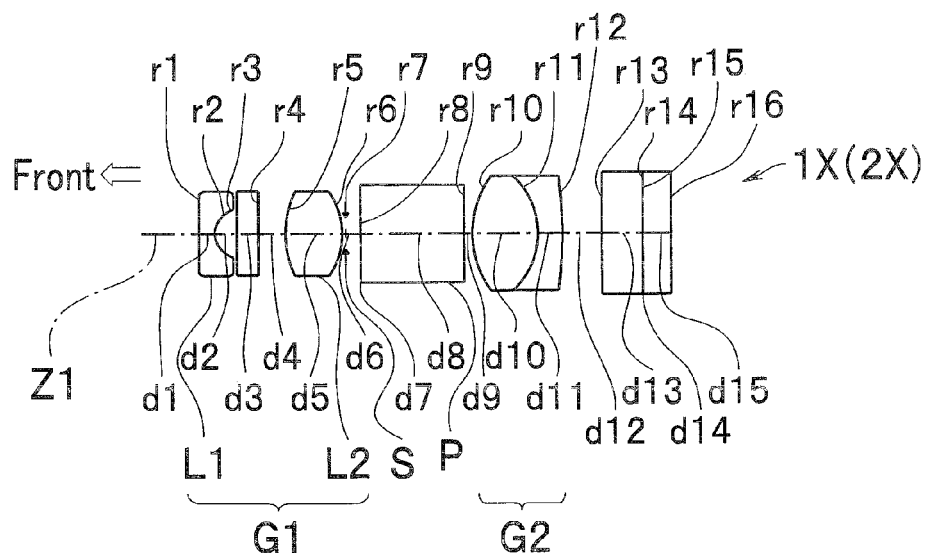
FIG. 62 is a diagram showing the optical configuration of an objective system of an oblique-viewing endoscope in Embodiment 22.
Figures 63A, 63B, 63C, 63D:
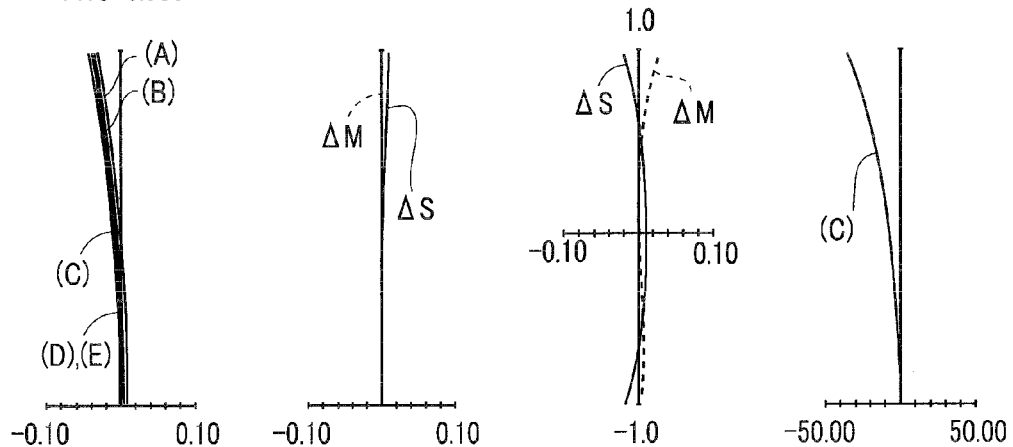
FIGS. 63A to 63D are aberration diagrams of the objective system of the oblique-viewing endoscope in Embodiment 22.

FIG. 62 shows the optical configuration of an objective system 2X of an oblique-viewing endoscope 1X in Embodiment 22. The objective system 2X in the present embodiment has a four-lens configuration, as does the objective system 2W in Embodiment 21.

In the objective system 2X in the present embodiment, however, glass materials having refractive indexes, the difference between which is small, 0.3, and comparatively easy to work are used in a cemented lens in a rear lens group G2. Although the radius of curvature of the joint surfaces of the cemented lens in the objective system 2X is small, the objective system 2X has good performance.

FIGS. 63A to 63D are aberration diagrams of the objective system 2X in the present embodiment.

Numeric data on the present embodiment is shown below.

| Surface No. | r | d | n(e) | v(e) |
|---|---|---|---|---|
| 1 | ∞ | 0.3574 | 1.88815 | 40.52 |
| 2 | 0.7476 | 0.4170 | 1. | |
| 3 | ∞ | 0.3574 | 1.52266 | 74.72 |
| 4 | ∞ | 0.5111 | 1. | |
| 5 | 2.5745 | 1.2486 | 1.48915 | 70.04 |
| 6 | −1.4230 | 0.0357 | 1. | |
| 7(Stop) | ∞ | 0.2502 | 1. | |
| 8 | ∞ | 2.4424 | 1.88815 | 40.52 |
| 9 | ∞ | 0.1549 | 1. | |
| 10 | 1.4765 | 1.2718 | 1.51825 | 63.93 |
| 11 | −1.1975 | 0.3596 | 1.85504 | 23.59 |
| 12 | −4.5495 | 0.5619 | 1. | |
| 13 | ∞ | 0.4766 | 1.51825 | 63.94 |
| 14 | ∞ | 0.0119 | 1.52233 | 52.71 |
| 15 | ∞ | 0.8340 | 1.50700 | 63.00 |
| 16 | ∞ | | | | f = 1, IH = 0.755, W = 50.002°
d/f = 1.734
d/IH = 2.297
D1/f = 2.476
D2/f = 2.623
D1/D2 = 0.944
|f1|/f = 0.842
f2/f = 2.088
G1f/f = 3.389
G2f/f = 3.577
G1f/G2f = 0.948

Embodiment 23

Figures 64, 65A, 65B, 65C, 65D:
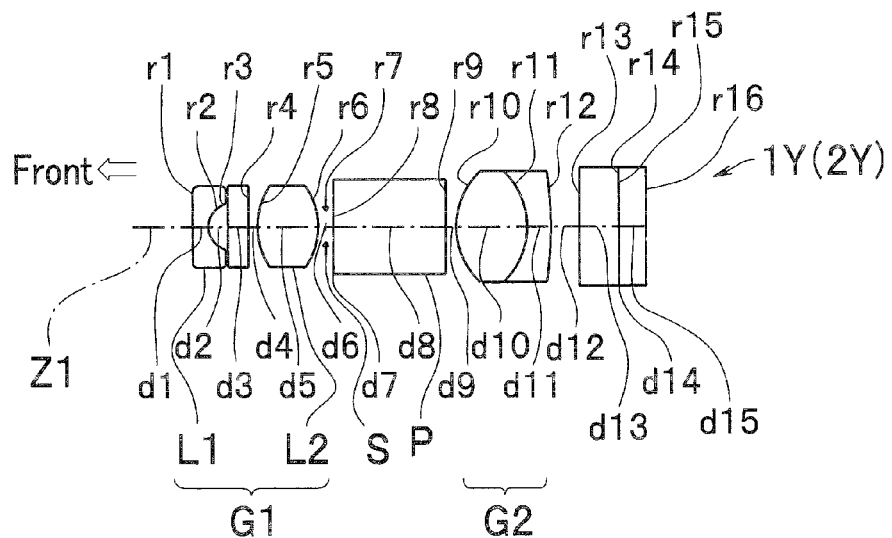
FIG. 64 is a diagram showing the optical configuration of an objective system of an oblique-viewing endoscope in Embodiment 23.
FIGS. 65A to 65D are aberration diagrams of the objective system of the oblique-viewing endoscope in Embodiment 23.

FIG. 64 shows the optical configuration of an objective system 2Y of an oblique-viewing endoscope 1Y in Embodiment 23. The objective system 2Y in the present embodiment has a four-lens configuration, as does the objective system 2W in Embodiment 21.

In the objective system 2Y in the present embodiment, glass materials other than that for a first lens L1 differ from those in the objective system 2W. In particular, the refractive index difference between the glass materials used for a cemented lens in a rear lens group G2 is large, 0.35. Therefore a chromatic aberration is suitably corrected.

FIGS. 65A to 65D are aberration diagrams of the objective system 2Y in the present embodiment.

Numeric data on the present embodiment is shown below.

| Surface No. | r | d | n(e) | v(e) |
|---|---|---|---|---|
| 1 | ∞ | 0.3426 | 1.88815 | 40.52 |
| 2 | 0.6315 | 0.3769 | 1. | |
| 3 | ∞ | 0.3426 | 1.52266 | 74.72 |
| 4 | ∞ | 0.1142 | 1. | |
| 5 | 1.7515 | 1.3784 | 1.51825 | 63.93 |
| 6 | −1.2749 | 0.1142 | 1. | |
| 7(Stop) | ∞ | 0.1142 | 1. | |
| 8 | ∞ | 2.6611 | 1.88815 | 40.52 |
| 9 | ∞ | 0.1485 | 1. | |
| 10 | 1.2301 | 1.1044 | 1.49846 | 81.14 |
| 11 | −1.1283 | 0.3391 | 1.85504 | 23.59 |
| 12 | −4.5472 | 0.4170 | 1. | |
| 13 | ∞ | 0.4568 | 1.51825 | 63.94 |
| 14 | ∞ | 0.0114 | 1.52233 | 52.71 |
| 15 | ∞ | 0.7994 | 1.50700 | 63.00 |
| 16 | ∞ | | | | f = 1, IH = 0.724, W = 50.002°
d/f = 1.786
d/IH = 2.467
D1/f = 2.034
D2/f = 2.324
D1/D2 = 0.875
|f1|/f = 0.711
f2/f = 1.686
G1f/f = 3.298
G2f/f = 3.235
G1f/G2f = 1.020

Embodiment 24

Figure 66:
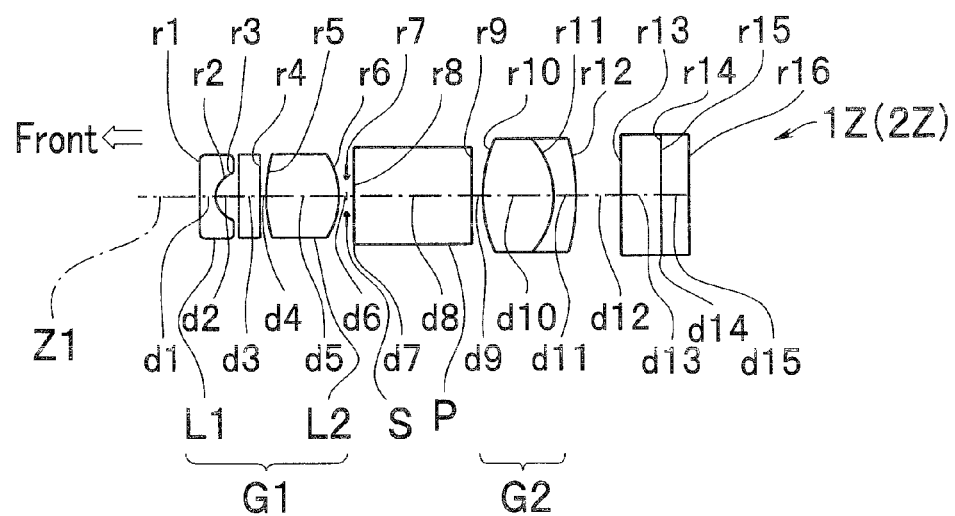
FIG. 66 is a diagram showing the optical configuration of an objective system of an oblique-viewing endoscope in Embodiment 24.
Figures 67A, 67B, 67C, 67D:
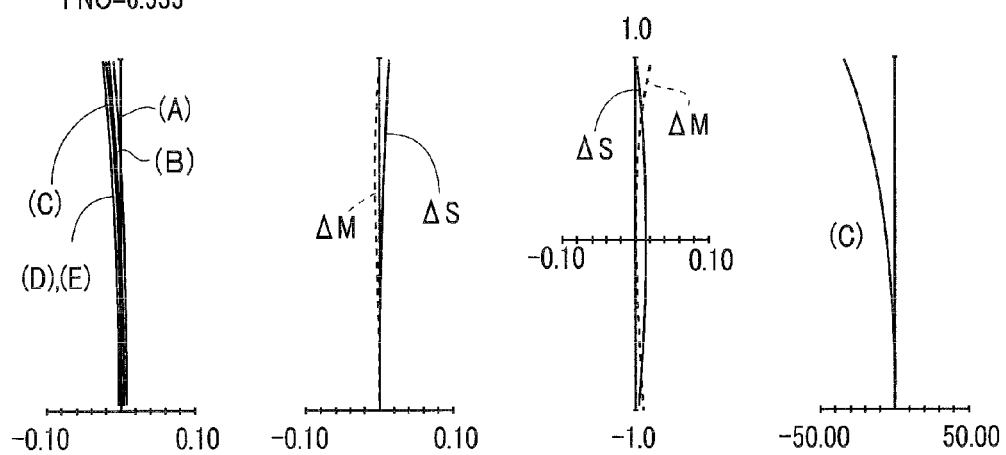
FIGS. 67A to 67D are aberration diagrams of the objective system of the oblique-viewing endoscope in Embodiment 24.

FIG. 66 shows the optical configuration of an objective system 2Z of an oblique-viewing endoscope 1Z in Embodiment 24. The objective system 2Z in the present embodiment has a four-lens configuration, as does the objective system 2W in Embodiment 21.

In the objective system 2Z in the present embodiment, however, a high-refractive-index material having a refractive index of 2 or more is used for a first lens L1. Because the high-refractive-index material is used, the first lens L1 has a large radius of curvature and lens working on the first lens L1 is easier to perform.

If a material having a high refractive index and high hardness, e.g., a crystalline material is used for the first lens L1, the lens outer surface is resistant to scratching. In the case of an endoscope in particular, lenses are small and, therefore, even a small scratch can be a cause of image nonuniformity or a flare. In the oblique-viewing endoscope 1Z using a high-hardness material for the first lens L1, however, the lens is resistant to scratching and, therefore, a good field of view can be maintained. Further, since a high-refractive-index material has a low Abbe constant and high dispersive power, the refractive index difference between glass materials used in a cemented lens can be set to a large value of 0.4 or more to enable suitably correcting a chromatic aberration.

FIGS. 67A to 67D are aberration diagrams of the objective system 2Z in the present embodiment.

Numeric data on the present embodiment is shown below.

| Surface No. | r | d | n(e) | v(e) |
|---|---|---|---|---|
| 1 | ∞ | 0.3646 | 2.18246 | 32.71 |
| 2 | 0.7931 | 0.4011 | 1. | |
| 3 | ∞ | 0.3646 | 1.52266 | 74.72 |
| 4 | ∞ | 0.1215 | 1. | |
| 5 | 4.3362 | 1.7162 | 1.77621 | 49.36 |
| 6 | −1.7401 | 0.1215 | 1. | |
| 7(Stop) | ∞ | 0.1215 | 1. | |
| 8 | ∞ | 2.8321 | 1.88815 | 40.52 |
| 9 | ∞ | 0.1580 | 1. | |
| 10 | 1.7950 | 1.1866 | 1.49846 | 81.14 |
| 11 | −1.3543 | 0.3609 | 1.93429 | 18.74 |
| 12 | −2.9819 | 0.8599 | 1. | |
| 13 | ∞ | 0.4861 | 1.51825 | 63.94 |
| 14 | ∞ | 0.0122 | 1.52233 | 52.71 |
| 15 | ∞ | 0.8507 | 1.50700 | 63.00 |
| 16 | ∞ | | | |

$f = 1$, $IH = 0.771$, $W = 49.999°$
$d/f = 1.901$
$d/IH = 2.466$
$D1/f = 2.138$
$D2/f = 2.889$
$D1/D2 = 0.740$
$|f1|/f = 0.671$
$f2/f = 1.825$
$G1f/f = 3.104$
$G2f/f = 3.710$
$G1f/G2f = 0.837$

In the objective system 2, an infrared cut filter or a color temperature converting filter for sensitivity correction to an image pickup device such as a CCD 20 may be disposed at the rear of the first lens L1. A special-function filter such as a laser cut filter for cutting off laser light from a TAG laser, a semiconductor laser or the like may also be disposed. Also, an interference film having an infrared cutting characteristic or a laser light rutting characteristic can be provided on a prism surface. As the above-described filter, an absorption-type filter, a reflection-type filter or an absorption-refraction-composite-type filter may be used. Also, a filter covered with an antireflection film may be used.

Further, the volume of an air layer formed on the first lens image surface side (rear side) can be reduced by providing a filter in the vicinity of the first lens L1. In this way, the influence of a fog due to dew condensation on the lens surface can be reduced. Further, joining the first lens L1 and the filter or sealing the first lens L1 and the filter in an airtight manner by means of a solder or the like is more effective.

It is preferred that, for a reduction in size of the rear lens group G2, the angle W of incidence of rays on the image pickup device at the maximum image height be set in a range of 0°<W<20°. If rays are obliquely incident in the above-described range on the image pickup device from the optical axis side, the ray height at the rear lens group G2 can be set low. Therefore the above-described setting enables reducing the lens diameter, hence, the size of the lens unit including the frame member. Particularly preferably, the ray incidence angle W is in the range from 3° to 10°. The ray incidence angle W is the angle of incidence of principal rays at the maximum image height when the medium is air.

Embodiment 25

Figure 68:
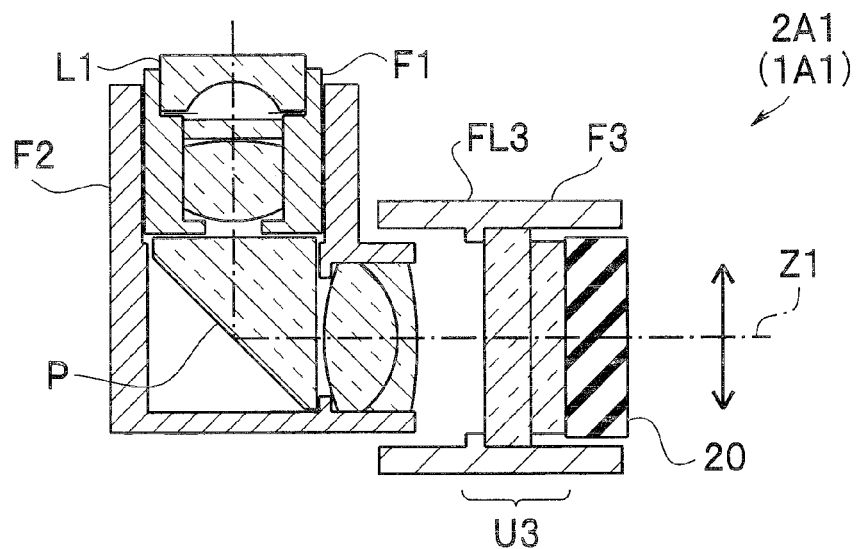
FIG. 68 is a diagram for explaining shift adjustment of a third lens unit, showing a section of a structure taken along an optical axis.

FIG. 68 shows the optical configuration of an objective system 2A1 of an oblique-viewing endoscope 1A1 in Embodiment 25, The objective system 2A1 has a first lens unit frame F1, a second lens unit frame F2 and a third lens unit frame F3. Optical adjustment can be performed in the objective system 2A1 including the third lens unit U3.

As shown in FIG. 68, the third lens unit U3 has a parallel filter FL3, which is a component part of the objective lens, and a CCD 20 attached to the third lens unit frame F3 through the parallel filter FL3. The third lens unit frame F3 and the second lens unit frame F2 are fitted to each other. A predetermined gap for adjustment, i.e., a clearance, is provided between fitting portions of the lens units fitted to each other. In the objective system 2A1, therefore, a shift adjustment in a direction perpendicular to the optical axis Z1 can be easily made between the third lens unit U3 and the other lens units U1 and U2. After adjustment, the gap for adjustment is filled with an adhesive to fix the frames.

That is, while the gap between the fitting portions in the known objective system is a small, less than 30 µm, a gap of, for example, 50 to 100 µm necessary for performing deviation angle adjustment is provided in the objective system 2A1. This shift mechanism for moving the entire third lens unit U3 is effective in deviation angle adjustment in the image pickup system and has no influence on other optical performance factors.

While shift adjustment of the third lens unit U3 alone has been described in the above, shift adjustment of the third lens unit U3 and, for example, rotational adjustment or tilt adjustment of the first lens unit U1 or shift adjustment of the second lens unit U2 may be performed in combination.

Embodiment 26

Figure 69:
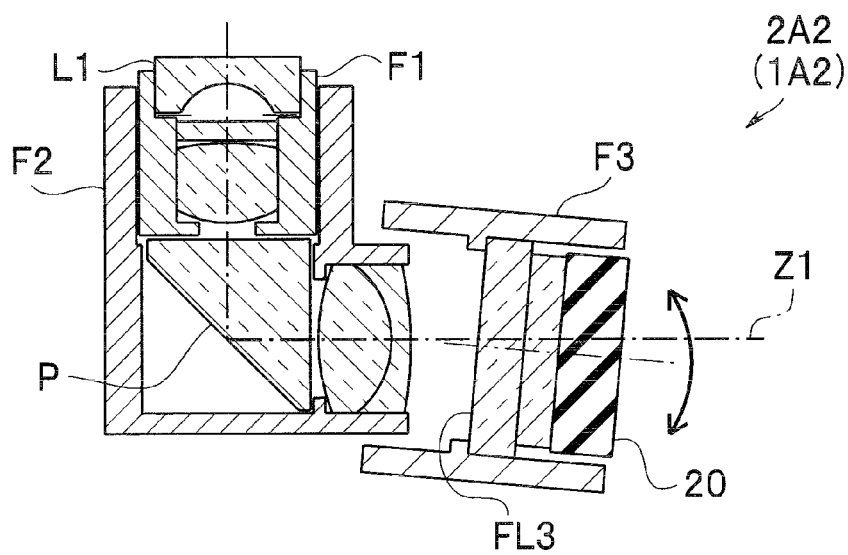
FIG. 69 is a diagram for explaining tilt adjustment of a third lens unit, showing a section of a structure taken along an optical axis.

FIG. 69 shows the optical configuration of an objective system 2A2 of an oblique-viewing endoscope 1A2 in Embodiment 26. The objective system 2A2 has a configuration similar to that of the objective system 2A1 in Embodiment 25. However, tilt adjustment of the third lens unit U3 in the objective system 2A2 relative to the other units U1 and U2 can be performed.

In some case, shift adjustment in the objective system 2A1, e.g., deviation angle adjustment requires a comparatively large adjustment gap. However, if the gap is large, filling with an adhesive material for bonding and fixing the frames to each other may be difficult to perform or the time required for filling may be increased. In contrast, in the case where tilt adjustment of the third lens unit U3 is performed, there is no need to increase the gap as in the case of shift adjustment. This is because, since tilting is performed on the basis of the frame fitting portions, the center position on the image pickup surface of the image pickup device disposed at a certain distance from the fitting portions can be largely shifted. However, if the image pickup surface is inclined excessively largely by tilt adjustment, an image peripheral portion is blurred to reduce the image quality. It is necessary to exercise care to avoid such a result.

While tilt adjustment of the third lens unit U3 has been mainly described, tilt adjustment of the third lens unit U3 and, for example, rotational adjustment or tilt adjustment of the first lens unit U1 or shift adjustment of the second lens unit U2 may be performed in combination.

Embodiment 27

Figure 70:
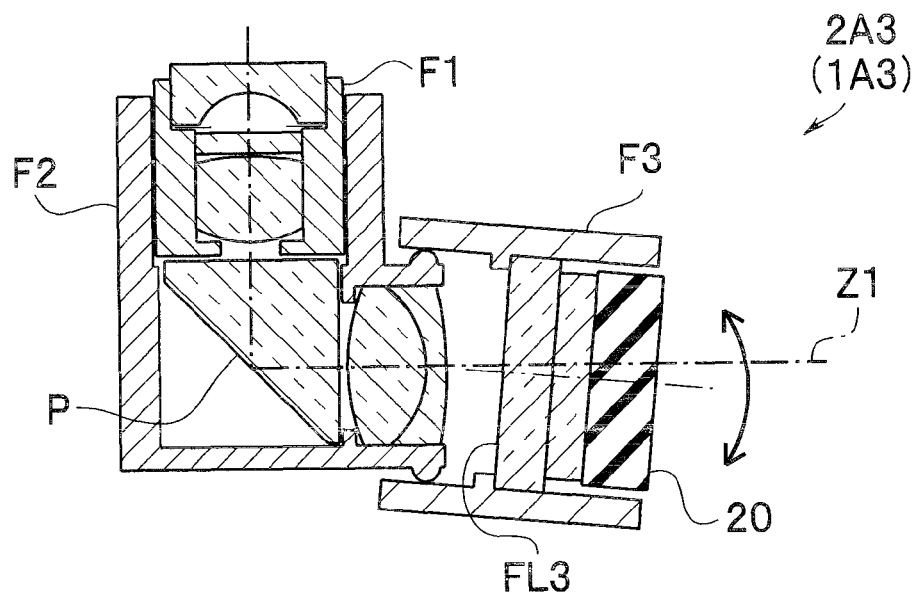
FIG. 70 is a diagram for explaining tilt adjustment of a third lens unit, showing a section of a structure taken along an optical axis.

FIG. 70 shows the optical configuration of an objective system 2A3 of an oblique-viewing endoscope 1A3 in Embodiment 27. The objective system 2A3 has a configuration similar to that of the objective system 2A2 in Embodiment 26. However, frame fitting portions of the second lens unit U2 and the third lens unit U3 fitted to each other have such a shape as to form a more easily tiltable structure. That is, the fitting portion of the second lens unit frame F2 has a projecting shape in its outside-diameter shape.

In the objective system 2A3, therefore, lens unit tilt adjustment can be easily performed while the second lens unit frame F2 and the third lens unit frame F3 are firmly fitted to each other. The projecting shape of the second lens unit frame F2 may be set so that the amount of tilt necessary for optical adjustment is obtained. Conversely to the above-described structure, the frame fitting portion of the third lens unit frame F3 may have a projecting shape in its inside-diameter shape to be fitted to a frame member outside-diameter portion of the second lens unit frame F2. Another structure may alternatively be used in which one of the two frames has a projecting shape while the other has a recessed shape.

In endoscopes, focus adjustment is ordinarily performed by means of a lens unit including an image pickup device. Therefore, the above-described structure has the advantage of enabling operations to be performed with stability in simultaneously performing focus adjustment and eccentricity adjustment.

Figure 71:
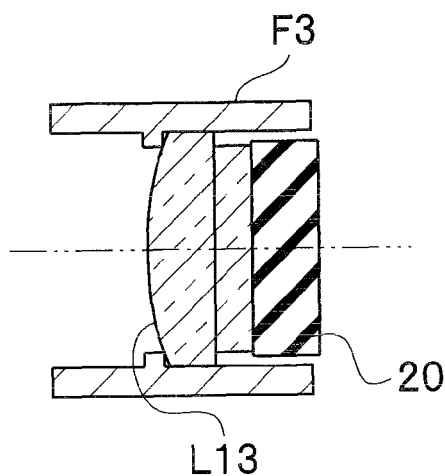
FIG. 71 is a diagram showing a section of the structure of a third lens unit taken along an optical axis.

In a case where a lens is disposed in the vicinity of a CCD 20 as in Embodiment 5 (FIG. 28) and in Embodiment 7 (FIG. 32), the third lens unit U3 has, for example, a lens L13 having a refractive power such as shown in FIG. 71 and the CCD 20. Also in this case, shift adjustment and tilt adjustment of the third lens unit U3 may be performed. In the case where the third lens unit U3 includes the lens L13 having a refractive power, there is a need to perform optical adjustment while paying attention to a reduction in image quality, in contrast to the case in Embodiment 25 or Embodiment 26. A reduction in image quality can be limited by balancedly performing adjustment of the third lens unit U3 along with adjustment with the other lens units.

As described above, optical adjustment can be easily performed in an oblique-viewing endoscope in which the third lens unit U3 and the other lens units (at least one of the first lens unit U1 and the second lens unit U2) can be made eccentric relative to each other. Also, optical adjustment can be easily performed in an oblique-viewing endoscope in which at least one of the first lens unit U1, the second lens unit U2 and the third lens unit U3 can be made eccentric relative to the other lens units.

In the above-described oblique-viewing endoscope, rotational adjustment of the second and third lens unit U2 and U3 cannot be performed because the second lens unit U2 having the prism P and the third lens unit U3 having the image pickup device have top-bottom/left-right directional anisotropies. Further, if the prism P is included in the first lens unit U1, rotational adjustment of the first lens unit U1 cannot be performed. Therefore, shift adjustment and tilt adjustment between the lens units are mainly performed for assembly adjustment.

FIG. 72 is a table showing the values of the condition expressions in each embodiment.

As described above, the oblique-viewing endoscope 1 according to the present invention has features described below.

In the following description, the lens distance between a front lens group G1 and a rear lens group G2 in an objective optical system 2 is d; the focal length of the entire objective optical system 2 is f; the maximum image height is IH; the lens distance from the first lens surface in the objective optical system 2 to the object-side surface of a visual field direction converting element is D1; the lens distance from the image-side surface of the visual field direction converting element to the image plane (the light detection surface of an image pickup device) is D2; the focal length of the front lens group G1 is G1$f$; the focal length of the rear lens group G2 is G2$f$; the focal length of a negative lens group in the front lens group is f1; the focal length of a positive lens group in the front lens group is f2; the visual field direction of the objective optical system 2, i.e., the oblique-viewing angle between a direction perpendicular to the longitudinal direction of the endoscope and an optical axis of the objective optical system 2, is θ1; the direction of illumination from an illumination optical system 3, i.e., the angle formed between a ray emitted from a center of a light emitting member and a direction perpendicular to the longitudinal direction of the endoscope after transmission of the ray through the illumination optical system 3, is θ2; and the distance between a center of the objective optical system 2, i.e., the optical axis, and a center of the illumination optical system 3, i.e., an optical axis, is L.

(1) An oblique-viewing endoscope includes an image pickup device; a front lens group having a positive refractive power; a visual field direction converting element disposed on the image pickup device side of the front lens group; and a rear lens group disposed on the image pickup device side of the visual field direction converting element and having a positive refractive power.

(2) The oblique-viewing endoscope described in (1) above further includes a first lens unit frame in which a first lens unit having the front lens group is disposed and a second lens unit frame in which a second lens unit having the rear lens group is disposed, and the first lens unit can be made eccentric relative to the second lens unit.

(3) The oblique-viewing endoscope described in (1) or (2) above further includes an illumination optical system disposed on the proximal end portion side of the oblique-viewing endoscope relative to the objective optical system.

(4) In the oblique-viewing endoscope described in any one of (1) to (3) above, the visual field direction converting element is a prism.

(5) In the oblique-viewing endoscope described in any one of (1) to (4) above, $1.1<d/f<2.1$ and $1.4<d/IH<3.0$ are satisfied.

(6) In the oblique-viewing endoscope described in any one of (1) to (5) above, $1.2<d/f<2.0$ and $1.5<d/IH<2.7$ are satisfied.

This facilitates adaptation for further increasing the field of view of the objective optical system 2 and reducing the size of the image pickup device.

(7) In the oblique-viewing endoscope described in any one of (1) to (6) above, $1.4<D1/f<3.1$ and $2.0<D2/f<3.9$ are satisfied.

The above condition expression indicates a configurational balance between the lens distances of the front lens group G1 and the rear lens group G2, and optimizes the lens outside diameter and the length of the entire system.

(8) In the oblique-viewing endoscope described in any one of (1) to (6) above, $1.6<D1/f<2.8$ and $2.3<D2/f<3.6$ are satisfied.

This facilitates adaptation for further increasing the field of view of the objective optical system 2 and reducing the size of the image pickup device.

(9) In the oblique-viewing endoscope described in any one of (1) to (8) above, $0.4<D1/D2<1.0$ is satisfied.

This condition expression relates to a lens distance ratio necessary for configuring the front group and the rear group about the visual field direction converting element. If this condition is satisfied, a distal end portion 5 can be configured without being increased in diameter.

(10) In the oblique-viewing endoscope described in any one of (1) to (9) above, $1.5<G1f/f<6.0$ and $3.0<G2f/f<6.0$ are satisfied.

This enables configuring the objective optical system 2 so that the outside diameter and the entire length are reduced, and the desired optical performance is secured.

(11) In the oblique-viewing endoscope described in any one of (1) to (10) above, $0.3 < G1f/G2f < 2.0$ is satisfied.

This condition expression relates to the refractive bower distribution between the front lens group G1 and the rear lens group G2 and enables configuring the objective optical system 2 so that the outside diameter and the entire length are reduced, and the desired optical performance is secured.

(12) In the oblique-viewing endoscope described in any one of (1) to (11) above, the front lens group has a negative lens group including at least a negative lens and a positive lens group including at least a positive lens.

(13) In the oblique-viewing endoscope described in any one of (1) to (12) above, $0.5 < |f1|/f < 1.1$ and $1.3 < f2/f < 2.8$ are satisfied.

This enables maintaining good lens workability and good optical performance.

(14) In the oblique-viewing endoscope described in any one of (1) to (12) above, $0.65 < |f1|/f < 1.0$ and $1.5\ f2/f < 2.5$ are satisfied.

This enables maintaining better lens workability and better optical performance.

(15) The oblique-viewing endoscope described in any one of (1) to (14) above includes a brightness stop disposed in the front lens group.

(16) In the oblique-viewing endoscope described in (2) above, the front lent group and a brightness stop are integrally configured in the first lens unit.

(17) In the oblique-viewing endoscope described in (2) or (16) above, the first lens unit can be adjusted by performing an operation for rotating the first lens unit relative to the second lens unit, an operation for shifting the first lens unit relative to the second lens unit, an operation for tilting the first lens unit relative to the second lens unit, or a combination of some of these operations.

(18) In the oblique-viewing endoscope described in (3) above, $0° \leq \theta1 \leq 20°$ and $0° \leq \theta2 \leq 25°$ are satisfied.

This enables optimizing the direction of illumination from the illumination optical system with respect to the visual field direction of the objective optical system 2 to obtain an image uniform in lightness.

(19) In the oblique-viewing endoscope described in (3) above, $3\ mm \leq L \leq 5\ mm$ is satisfied.

By arranging the objective optical system and the illumination optical system in the above range, the influence of a parallax at the time of closeup observation can be reduced and an image uniform in lightness in the scope of observation can be obtained.

According to the present invention, as described above, a small-size lens configuration most suitable for an oblique-viewing endoscope having improved observation performance and capable of reducing the size of an image pickup device such as a CCD 20 and increasing the number of pixels of the image pickup device while securing the desired strength of a lens frame can be provided, and an oblique-viewing endoscope 1 having a distal end portion 5 reduced in diameter can be provided.

Also, according to the present invention, an oblique-viewing endoscope 1 can be provided which is capable of preventing occurrence of a fog in an objective optical system 2 by fixing a distal end lens (first lens L1) and a lens frame F in an objective optical system 2 to each other without a gap, has a structure capable of implementing a method for adjustment of a novel structure and has stabilized optical performance.

Also, according to the present invention, an oblique-viewing endoscope 1 can be provided which is arranged to reduce the influence of an image cut-off due to a forceps rising base 6 or the like while enabling improving observation performance and treatment performance, and which is capable of applying sufficient illumination light even to a visual field peripheral portion even when the field of view for observation is increased, that is, has a good luminous intensity distribution such that even a visual field peripheral portion is sufficiently light.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope for oblique viewing comprising:
   an image pickup device;
   a front lens group having a positive refractive power;
   a visual field direction converting element disposed on the image pickup device side of the front lens group; and
   a rear lens group disposed on the image pickup device side of the visual field direction converting element and having a positive refractive power;
   wherein if the lens distance between the front lens group and the rear lens group in an objective optical system having the visual field direction converting element is d; the focal length of the entire system is f; the maximum image height is IH, $1.1 < d/f < 2.1$ and $1.4 < d/IH < 3.0$ are satisfied.

2. An endoscope for oblique viewing comprising:
   an image pickup device;
   a front lens group having a positive refractive power;
   a visual field direction converting element disposed on the image pickup device side of the front lens group; and
   a rear lens group disposed on the image pickup device side of the visual field direction converting element and having a positive refractive power;
   wherein if the lens distance from the first lens surface in the objective optical system having the visual field direction converting element to the object-side surface of the visual field direction converting element is D1; the lens distance from the image-side surface of the visual field direction converting element to the image plane is D2; and the focal length of the entire objective optical system is f, $1.4 < D1/f < 3.1$ and $2.0 < D2/f < 3.9$ are satisfied.

3. The endoscope for oblique viewing according to claim 2, wherein if the lens distance from the first lens surface in the objective optical system having the visual field direction converting element to the object-side surface of the visual field direction converting element is D1; and the lens distance from the image-side surface of the visual field direction converting element to the image plane is D2, $0.4 < D1/D2 < 1.0$ is satisfied.

4. An endoscope for oblique viewing comprising:
   an image pickup device;
   a front lens group having a positive refractive power;
   a visual field direction converting element disposed on the image pickup device side of the front lens group; and
   a rear lens group disposed on the image pickup device side of the visual field direction converting element and having a positive refractive power;
   wherein if the focal length of the front lens group is G1f; the focal length of the rear lens group is G2f; and the focal length of the entire objective optical system is f, $1.5 < G1f/f < 6.0$ and $3.0 < G2f/f < 6.0$ are satisfied.

5. The endoscope for oblique viewing according to claim 4, wherein if the focal length of the front lens group is G1$f$; the focal length of the rear lens group is G2$f$; and the focal length of the entire objective optical system is f, 0.3<G1$f$/G2$f$<2.0 is satisfied.

6. An endoscope for oblique viewing comprising:
an image pickup device;
a front lens group having a positive refractive power;
a visual field direction converting element disposed on the image pickup device side of the front lens group; and
a rear lens group disposed on the image pickup device side of the visual field direction converting element and having a positive refractive power;
wherein the front lens group has a negative lens group including at least a negative lens and a positive lens group including at least a positive lens and if the focal length of the negative lens group in the front lens group is f1; the focal length of the positive lens group in the front lens group is f2; and the focal length of the entire objective optical system is f, 0.5<|f1|/f<1.1 and 1.3<f2/f<2.8 are satisfied.

7. The endoscope for oblique viewing according to claim 1, wherein the visual field direction converting element comprises a prism.

8. The endoscope for oblique viewing according to claim 7, further comprising a brightness stop disposed in the front lens group.

9. The endoscope for oblique viewing according to claim 8, wherein the front lens group and the brightness stop are integrally configured in the first lens unit.

10. The endoscope for oblique viewing according to claim 1, further comprising an illumination optical system disposed on the proximal end portion side of the endoscope for oblique viewing relative to the objective optical system.

11. The endoscope for oblique viewing according to claim 10, wherein if an oblique-viewing angle is θ1 and an illumination angle is θ2, 0°≤θ1≤20° and 0°≤θ2≤25° are satisfied.

12. The endoscope for oblique viewing according to claim 10, wherein if the distance between a center of the objective optical system and a center of the illumination optical system (optical axis) is L, 3 mm≤L≤5 mm is satisfied.

13. The endoscope for oblique viewing according to claim 1, further comprising a first lens unit frame in which a first lens unit having the front lens group is disposed, and a second lens unit frame in which a second lens unit having the rear lens group is disposed, wherein the first lens unit can be made eccentric relative to the second lens unit.

14. The endoscope for oblique viewing according to claim 2, further comprising a first lens unit frame in which a first lens unit having the front lens group is disposed, and a second lens unit frame in which a second lens unit having the rear lens group is disposed, wherein the first lens unit can be made eccentric relative to the second lens unit.

15. The endoscope for oblique viewing according to claim 4, further comprising a first lens unit frame in which a first lens unit having the front lens group is disposed, and a second lens unit frame in which a second lens unit having the rear lens group is disposed, wherein the first lens unit can be made eccentric relative to the second lens unit.

16. The endoscope for oblique viewing according to claim 6, further comprising a first lens unit frame in which a first lens unit having the front lens group is disposed, and a second lens unit frame in which a second lens unit having the rear lens group is disposed, wherein the first lens unit can be made eccentric relative to the second lens unit.

17. The endoscope for oblique viewing according to claim 13, wherein optical adjustment of at least one of the first lens unit and the second lens unit can be performed by performing an operation for rotating the one of the lens units relative to the other lens unit, an operation for shifting the one of the lens units relative to the other lens unit, an operation for tilting the one of the lens units relative to the other lens unit, or a combination of some of the operations.

18. The endoscope for oblique viewing according to claim 14, wherein optical adjustment of at least one of the first lens unit and the second lens unit can be performed by performing an operation for rotating the one of the lens units relative to the other lens unit, an operation for shifting the one of the lens units relative to the other lens unit, an operation for tilting the one of the lens units relative to the other lens unit, or a combination of some of the operations.

19. The endoscope for oblique viewing according to claim 15, wherein optical adjustment of at least one of the first lens unit and the second lens unit can be performed by performing an operation for rotating the one of the lens units relative to the other lens unit, an operation for shifting the one of the lens units relative to the other lens unit, an operation for tilting the one of the lens units relative to the other lens unit, or a combination of some of the operations.

20. The endoscope for oblique viewing according to claim 16, wherein optical adjustment of at least one of the first lens unit and the second lens unit can be performed by performing an operation for rotating the one of the lens units relative to the other lens unit, an operation for shifting the one of the lens units relative to the other lens unit, an operation for tilting the one of the lens units relative to the other lens unit, or a combination of some of the operations.

21. The endoscope for oblique viewing according to claim 13, further comprising a third lens unit frame in which a third lens unit having the image pickup device is disposed, wherein at least one of the first lens unit, the second lens unit and the third lens unit can be made eccentric relative to the other lens units.

22. The endoscope for oblique viewing according to claim 14, further comprising a third lens unit frame in which a third lens unit having the image pickup device is disposed, wherein at least one of the first lens unit, the second lens unit and the third lens unit can be made eccentric relative to the other lens units.

23. The endoscope for oblique viewing according to claim 15, further comprising a third lens unit frame in which a third lens unit having the image pickup device is disposed, wherein at least one of the first lens unit, the second lens unit and the third lens unit can be made eccentric relative to the other lens units.

24. The endoscope for oblique viewing according to claim 16, further comprising a third lens unit frame in which a third lens unit having the image pickup device is disposed, wherein at least one of the first lens unit, the second lens unit and the third lens unit can be made eccentric relative to the other lens units.

25. The endoscope for oblique viewing according to claim 15, wherein optical adjustment of at least one of the first lens unit, the second lens unit and the third lens unit can be performed by performing an operation for rotating the one of the lens units relative to the other lens units, an operation for shifting the one of the lens units relative to the other lens units, an operation for tilting the one of the lens units relative to the other lens units, or a combination of some of the operations.

26. The endoscope for oblique viewing according to claim 2, wherein the visual field direction converting element comprises a prism.

27. The endoscope for oblique viewing according to claim 26, further comprising a brightness stop disposed in the front lens group.

28. The endoscope for oblique viewing according to claim 4, wherein the visual field direction converting element comprises a prism.

29. The endoscope for oblique viewing according to claim 28, further comprising a brightness stop disposed in the front lens group.

30. The endoscope for oblique viewing according to claim 6, wherein the visual field direction converting element comprises a prism.

31. The endoscope for oblique viewing according to claim 30, further comprising a brightness stop disposed in the front lens group.

32. The endoscope for oblique viewing according to claim 2, further comprising an illumination optical system disposed on the proximal end portion side of the endoscope for oblique viewing relative to the objective optical system.

33. The endoscope for oblique viewing according to claim 32, wherein if an oblique-viewing angle is θ1 and an illumination angle is θ2, $0°≤θ1≤20°$ and $0°≤θ2≤25°$ are satisfied.

34. The endoscope for oblique viewing according to claim 32, wherein if the distance between a center of the objective optical system and a center of the illumination optical system (optical axis) is L, $3\ mm≤L≤5\ mm$ is satisfied.

35. The endoscope for oblique viewing according to claim 4, further comprising an illumination optical system disposed on the proximal end portion side of the endoscope for oblique viewing relative to the objective optical system.

36. The endoscope for oblique viewing according to claim 35, wherein if an oblique-viewing angle is θ1 and an illumination angle is θ2, $0°≤θ1≤20°$ and $0°≤θ2≤25°$ are satisfied.

37. The endoscope for oblique viewing according to claim 35, wherein if the distance between a center of the objective optical system and a center of the illumination optical system (optical axis) is L, $3\ mm≤L≤5\ mm$ is satisfied.

38. The endoscope for oblique viewing according to claim 6, further comprising an illumination optical system disposed on the proximal end portion side of the endoscope for oblique viewing relative to the objective optical system.

39. The endoscope for oblique viewing according to claim 38, wherein if an oblique-viewing angle is θ1 and an illumination angle is θ2, $0°≤θ1≤20°$ and $0°≤θ2≤25°$ are satisfied.

40. The endoscope for oblique viewing according to claim 38, wherein if the distance between a center of the objective optical system and a center of the illumination optical system (optical axis) is L, $3\ mm≤L≤5\ mm$ is satisfied.

* * * * *